(12) United States Patent
Hynynen et al.

(10) Patent No.: US 6,511,444 B2
(45) Date of Patent: Jan. 28, 2003

(54) TRANSMYOCARDIAL REVASCULARIZATION USING ULTRASOUND

(75) Inventors: Kullervo Hynynen, Medfield, MA (US); Douglas R. Daum, Belmont, MA (US); Mark T. Buchanan, Tucson, AZ (US); Todd Fjield, Cambridge, MA (US)

(73) Assignee: Brigham and Women's Hospital, Boston, MA (US)

( * ) Notice: Subject to any disclaimer, the term of this patent is extended or adjusted under 35 U.S.C. 154(b) by 0 days.

(21) Appl. No.: 09/523,989

(22) Filed: Jan. 31, 2000

(65) Prior Publication Data

US 2002/0151777 A1 Oct. 17, 2002

Related U.S. Application Data

(63) Continuation of application No. 09/048,864, filed on Mar. 26, 1998, now abandoned.
(60) Provisional application No. 60/074,969, filed on Feb. 17, 1998.

(51) Int. Cl.[7] ............................................. A61B 17/22
(52) U.S. Cl. ........................................................ 601/2
(58) Field of Search ............................. 600/439; 601/2, 601/3, 4; 604/22

(56) References Cited

U.S. PATENT DOCUMENTS

| | | | |
|---|---|---|---|
| 5,694,936 A | * 12/1997 | Fujimoto et al. | 128/660.03 |
| 5,928,169 A | * 7/1999 | Schatzle et al. | 601/2 |
| 6,042,556 A | * 3/2000 | Beach et al. | 601/3 |
| 6,086,534 A | * 7/2000 | Kesten et al. | 600/439 |
| 6,135,971 A | * 10/2000 | Hutchinson et al. | 601/3 |

FOREIGN PATENT DOCUMENTS

WO    WO 00/33913    * 5/2000    ............ A61N/1/00

OTHER PUBLICATIONS

He Ding Sheng et al. in Preliminary Results Using Ultrasound Energy for Ablation of the Ventricular Myocardium in Dogs, American Journal of Cardiology (May 15, 1994).*

He Ding Sheng et al., Comparison of Several Ultrasonic Frequencies for Cardiac Ablation, Circulation 90 (4 Part 2) (Nov. 14, 1994).*

Nadine Barrie Smith and Kullerno Hynynen in The Feasibility of using Ultrasound for Transmyocardial Revascularization, Ultrasound in Medicine & Biology (May 11, 1998).*

* cited by examiner

Primary Examiner—Marvin M. Lateef
Assistant Examiner—Eleni Mantis Mercader
(74) Attorney, Agent, or Firm—Lahive & Cockfield, LLP

(57) ABSTRACT

A method and apparatus for performing transmyocardial revascularization using ultrasound is disclosed. The apparatus includes a phased array ultrasonic device that includes a plurality of ultrasonic transducer elements which are controlled using a feedback control system so that each ultrasonic transducer element produces an ultrasonic wave of particular power and phase in order to achieve constructive interference at a desired acoustic focus. The constructive interference creates high pressure amplitudes for vaporizing the target tissue at the focus. A method is provided for vaporizing target tissue for which a plurality of ultrasonic transducers are focused so as to provide constructive interference within the target tissue. The ultrasonic beams are launched and produce a rapid rise in tissue temperature that will vaporize the target tissue within the focal zone.

18 Claims, 22 Drawing Sheets

TRANSMYOCARDIAL REVASCULARIZATION USING ULTRASOUND

This application continuation application of Ser. No. 09/048,864 filed on Mar. 26, 1998, abandoned, which in turn claims priority to provisional application of Ser. No. 60/074,969 filed on Feb. 17, 1998, expired. The contents of all of the aforementioned application(s) are hereby incorporated by reference.

BACKGROUND OF THE INVENTION

This invention relates generally to ultrasonic systems used for the vaporization of tissue, and more particularly to a phased array ultrasonic system used for creating channels within organs by ablating tissue.

Cardiac ischemia is a condition in which oxygenated blood is reduced or cutoff to a section of the heart, usually as the result of cholesterol-laden plaque narrowing the coronary arteries and preventing blood flow. Untreated ischemia may lead to ischemic heart disease often with disabling angina. Angina is severe chest pain caused by insufficient oxygenated blood reaching the heart often during times of exercise or emotional stress. Untreated ischemic heart disease with its associated angina may lead to heart attacks and death or in somewhat less severe cases to a great reduction in the quality of life for the patient.

There are currently three treatments for the treatment of cardiac ischemic disease and angina. The first therapy is pharmacological. Drugs for reducing cholesterol and for managing the pain of the patient are administrated in conjunction with exercise in order to increase the amount of oxygenated blood reaching the cardiac tissue. The second treatment is balloon angioplasty. In this treatment a catheter is worked into the coronary arteries carrying with it a balloon, when the catheter reaches the portions of the coronary arteries that are clogged with plaque, the balloon is expanded compressing the plaque and opening the coronary artery wider in order to allow greater blood flow. The third current treatment is a coronary graft by-pass operation. The coronary by-pass operation is one where new arteries are grafted around the clogged coronary arteries creating new, unobstructed, blood passageways.

Recently a new treatment for cardiac ischemic disease has been developed called transmyocardial revascularization (TMR). In TMR tiny channels, approximately 1 mm in diameter, are drilled through the heart muscle to allow oxygenated blood from the left ventricle to flow through these channels into the damaged muscle tissue to bring oxygenated blood to those areas. Currently, TMR utilizes high powered lasers to drill these holes in the cardiac muscle. TMR is an invasive procedure since currently TMR techniques still require the chest to be opened sufficiently to visualize the heart. The laser is then used to drill holes from outside of the heart muscle through the entire heart muscle into the left ventricle. Although current studies show that the outer portion of the drilled channel does heal, more tissue is still damaged than is needed to bring oxygenated blood to the damaged tissues. In addition, the lasers used for TMR are expensive to obtain and to operate. In another method of laser TMR, the laser is threaded into the left ventricle and the channels are drilled into the wall directly. While this method does not destroy more tissue than necessary, it is still invasive, in that the laser is threaded through the circulatory system into the interior of the heart, and in particular to the left ventricle chamber of the heart, in order to be proximate to the target areas.

While TMR is a new procedure, the use of lasers to vaporize tissue, and the problems associated therewith, are not new. The present invention is superior to using lasers to vaporize tissue, since a laser can destroy more tissue than is necessary, or can perforate tissue causing additional complications, whereas the present invention is more easily controlled.

Other methods that exist to destroy tissue have other problems as well. For example, direct current cardiac tissue ablation requires a catheter to be inserted into the interior of the heart and 2,000 to 4,000 volts of electricity are applied to the target tissue over several milliseconds. In addition to being invasive, the severe muscle contractions which result, require the patient to be under general anesthesia.

RF and microwave ablation of cardiac tissue is invasive since it requires a catheter inserted into the interior of the heart. In addition the energy is difficult to focus and the size of the target tissue to be ablated is limited due to the lower energy available.

There are two methods currently used to deliver ultrasonic energy to target tissue. The first is to use a catheter with an ultrasonic transducer or transducer array on the tip. The catheter must be inserted into the interior of the heart and be in close proximity to the target tissue, due to the inability to narrowly focus the beam. Although phased array catheter probes have been discussed in the literature there are none commercially available. In addition, the size of the probe will limit the number of available phased array elements. The fewer the number of elements, the wider the main lobe of the antenna becomes. This will result in heating a wider area of tissue and hence cause the collateral destruction of healthy tissue during treatment. In addition more energy will be in the sidelobes of the phased array which will reduce the efficiency and possibly damage collateral tissue as well.

The second method of delivering ultrasonic energy is the use of an external ultrasonic transducer, having a phased array antenna in conjunction with a hydrophone array. The hydrophone is invasively placed to provide detection of the ultrasonic energy to determine its focus point. The hydrophone measurement provides the necessary feedback to adjust the beam focus properly so as to limit collateral tissue damage. However, the hydrophone array must be placed proximate to the target tissue so as to be effective.

Vaporization of tissue using ultrasound has not been described in the prior art. Although it has been known generally in the art that small cavities are formed in tissue during ultrasonic exposures with high power. However, there have not been any attempts to control this cavity and use it for tissue removal. In addition, the exposure parameters that cause desired, controlled tissue vaporization have not been known. There is a need for an apparatus to produce the energy required at the appropriate frequency to create tissue vaporization.

Therefore what is needed is an ultrasonic apparatus capable of producing sufficient pressure at the acoustic focus to vaporize tissue, and an ultrasound phased array with a feedback control system capable of measuring and controlling the power and phase from each individual array element such that TMR channels are created noninvasively within the myocardium by vaporizing tissue at the acoustic focus of the phased array. This will enable tissue to be vaporized without opening the patient's body in order to actually see the tissue to be vaporized without having to invasively thread a catheter or hydrophone array into the patient's body.

SUMMARY OF THE INVENTION

According to the invention, phased array ultrasonic devices are provided for use in vaporizing tissue noninvasively during medical treatment. The device includes a plurality of ultrasonic transducer elements which transmit ultrasonic waves each having a particular power and phase. The control of an individual ultrasonic transducer element to produce ultrasonic energy having a particular power and phase is needed to achieve constructive interference at the desired acoustic focus, and is achieved by a focusing means that is responsive to a feedback signal. This constructive interference creates high pressure amplitudes for vaporizing the target tissue at the focus. The individual ultrasonic transducer elements are supplied energy by a channel driver element that is responsive to the focusing means.

To achieve this desired acoustic focus, in one embodiment, the driver element is responsive to a focusing element and feedback means to properly drive the ultrasonic transducer elements. The focusing element comprises a controller that determines an operating parameter of the ultrasonic transducer element. The controller is responsive to the feedback signal and in the preferred embodiment determines the phase and power to be transmitted by each individual ultrasonic transducer and provides a control signal to each channel driver element of the corresponding ultrasonic transducer element. The controller in being responsive to the feedback signal, also provides the necessary control signals to the driver element to adjust the power and phase of each individual ultrasonic transducer element relative to other array elements in order to create the desired acoustic focus.

Each ultrasonic transducer has a portion of either the signal driving the ultrasonic transducer, or the ultrasonic energy emanating from the ultrasonic transducer, fedback so that its power is measured and its phase determined. These measurements are then provided in a feedback manner to the controller. The controller provides any necessary adjustment to the driver element for the ultrasonic transducer to correct any aberration from the desired operating parameter. In this way, the desired wave front of ultrasonic energy is generated and corrections of the wave front are made automatically to insure that only the desired target tissue volume is heated and vaporized. In addition, the phase and power measurements are made without the need for invasively including a hydrophone array within the patient's body cavity.

In one aspect of the present invention, the driver element is a Class D/E switching amplifier. The Class D/E amplifier connects the ultrasonic transducer element to a power supply by switching at a particular frequency, and provides a high efficiency power transfer. In a preferred aspect of the present invention, high power MOSFET transistors are used as the switching elements in the Class D/E amplifiers.

In another aspect of the present invention, the controller comprises a power controller for controlling the level of DC power available to the driver element. The power controller is a switching DC/DC power regulator that provides power to the class D/E amplifier at a power level selected by the switching frequency. By varying the switching power regulator switching frequency, the power level to the Class D/E amplifier may be controlled and fine tuned according to the feedback signal and control inputs.

In yet another aspect the controller comprises a phase controller. The phase controller comprises a phase shifter that is the combination of a programmable delay chip and a counter. These chips combine to provide the total resolution of phase control of the transmitted ultrasonic wave. In addition, a phase locked loop is used as a phase detector and to ensure coherence between the phase shifter and the signal driving the power converter so that the proper wave is produced.

In another aspect of the present invention, a feedback means provides a feedback signal that is representative of the output signal. The feedback signal comprises a phase measurement and power measurement from either the input to, or the output from, a corresponding ultrasonic transducer. The feedback signal is fedback to a controller that will adjust a control signal provided to the mean for driving so as to correct the phase and power at the electrical signal provided to the corresponding ultrasonic transducer element.

A method is provided for vaporizing target tissue in which a plurality of ultrasonic transducers are focused so as to provide constructive interference within the target tissue. The ultrasonic beams are launched and produce fast tissue temperature rise and vaporizes the target tissue within the focal zone.

In another aspect, the invention features a method for forming a cavity in cardiac tissues in a subject. The methods include focusing an ultrasound beam on the target tissue, where the cavity is to be formed, thereby creating the cavity by vaporizing the target tissue.

In preferred embodiment the cavity is a channel connecting the left ventricle and tissue in the myocardium.

In preferred embodiment the method is noninvasive, i.e., the transducer is located outside the body of the subject.

In preferred embodiment a device described herein is used to form the cavity.

In preferred embodiment the energy delivered is sufficient to vaporize target tissue.

The present invention provides a safer and highly efficacious treatment than the prior art. The present invention is much safer than by-pass surgery in that the sternum is not split and the heart itself is not stopped for the duration of the operation. In addition, the present invention may provide a shorter recovery time and is not as costly a procedure to undertake.

While a preferred embodiment is described, it should be apparent that many modifications and variations are possible, all of which fall within the scope of the Detailed Description and Claims which follow.

BRIEF DESCRIPTION OF THE DRAWINGS

These and other features and advantages of the present invention will be better understood by reading the following detailed description taken together with the following drawings wherein.

DETAILED DESCRIPTION

Figure 1:
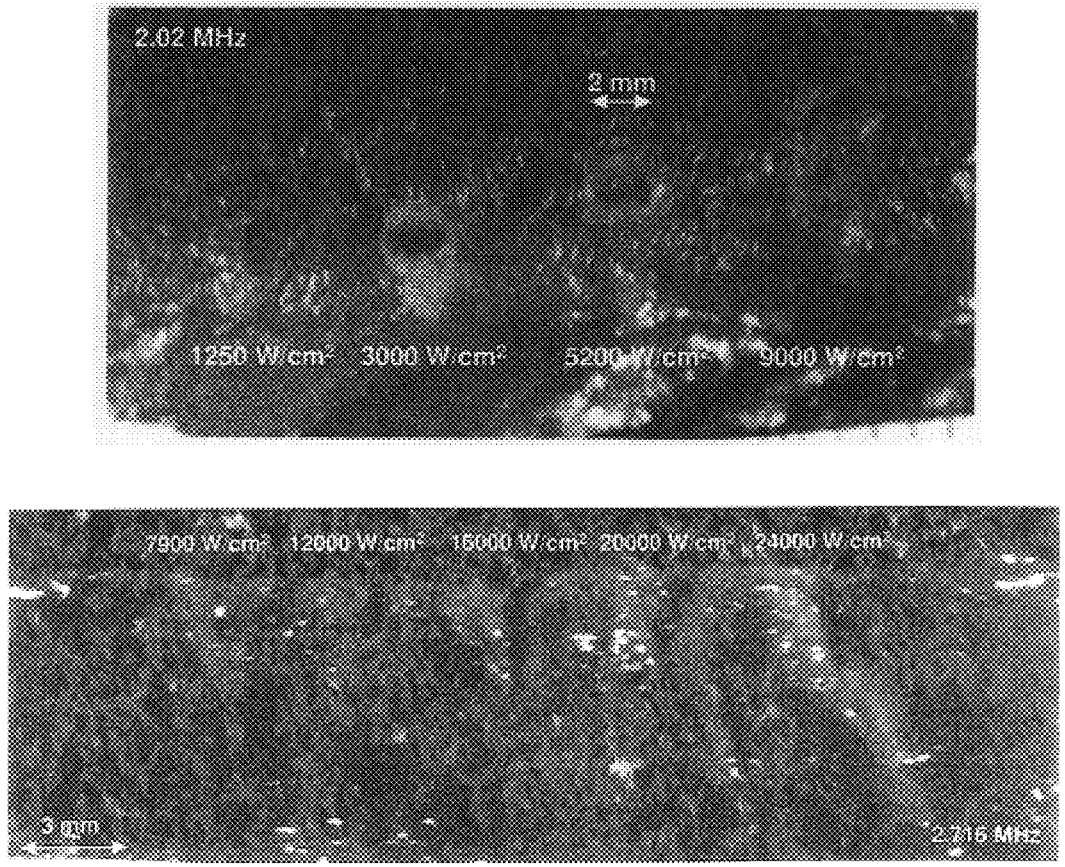
FIG. 1 shows a photograph of ultrasonically formed cavities in beef hearts.

In accordance with the current invention, a method and apparatus is described that advantageously creates channels in the left ventricular wall of the heart to improve blood supply to a damaged myocardium. Conventional techniques for creating these channels have included laser energy delivered by a fiber that is placed next to the cardiac wall. A short energy pulse is delivered that vaporizes the tissue. Channels of about one millimeter in diameter are formed to the cardiac wall with this technique It has been discovered by the current inventors that ultrasonic energy can be focused and sufficiently controlled to vaporize cardiac tissue and thus create the channels within the myocardium for transmyocardial revascularization. The novel method involves the delivery of ultrasonic energy by a plurality of ultrasonic transducers arranged in a phase array to elevate tissue temperature rapidly at the target location through constructive interference of the ultrasonic waves. Alternatively, the formation of gas bubbles may be utilized to mechanically disintegrate the tissue when the pressure amplitudes are high enough.

Myocardial revascularization through ultrasound techniques offers the following advantages over conventional laser systems. Ultrasound can be focused through tissue and thus the channel formation does not require physical contact with the transducer. This makes formation of channels of roughly any shape or geometry possible which would theoretically allow more optimal channel networks to be experimentally tested and clinically used. Furthermore, the ability to focus ultrasound allows for a completely non-invasive procedure which may be guided through imaging with MRI, CT or diagnostic ultrasound technology. Finally, ultrasound can be generated with equipment that is potentially less expensive than current laser systems.

The method of performing transmyocardial revascularization through ultrasonic techniques involves the steps of providing a plurality of ultrasonic transducers in a phased array configuration to deliver ultrasonic energy at a target location within the myocardium, focusing the individual transducers of the array to produce constructive interference of the ultrasonic wave fronts at the target location, and adjusting the power and phase output of the ultrasonic transducers through feedback to provide sufficient ultrasonic energy at the target location to vaporize the cardiac tissue.

In Vitro Experiments:

In experiments relating to transmyocardial revascularization using ultrasonic energy, ultrasound fields were generated by a focused ultrasound transducer operating at two different frequencies (0.6 MHz and 2.02 MHz). The transducer was 100 mm in diameter with a 80 mm radius of curvature. The RF-signal feeding the transducers was induced by a frequency generator (Wavetek Inc., model 271) and amplified by an RF-amplifier (ENI Inc., model MOA500). A power meter (Hewlett Packard 438A) and dual directional coupler (Werlatone C2625) were used to monitor the forward and reflected power to the transducer matching network. The electrical impedance of the transducer was matched to the output impedance of the amplifiers by an external matching network. The frequency generator was triggered to give short pulses by a portable PC computer via a parallel port.

The sonications were performed in degassed, deionized water in a plastic tank the walls of which were lined by rubber mats. The transducer was mounted on a metal arm connected to a mechanical positioning device that allowed the transducer to be positioned in three degrees of freedom with the resolution of 0.01 mm. This resolution was reached by mounting digital calipers on the positioning device. The transducer was aimed to the surface of the water through a hole in a plastic plate that supported the heart.

The total acoustical power as a function of the applied electrical power (forward-reflected) was measured using a radiation force technique with a lab balance as the force detector. The absolute intensity in the waterbath was measured using a PVDF membrane hydrophone. The relative intensity distributions were obtained by scanning a thermocouple probe coated with a bead of silicone rubber in the field.

Fresh beef hearts (3) were obtained within minutes of death. The hearts were removed and placed in saline solution. The sonications were performed within 3–4 hours. The heart was placed on a plastic holder that had an open window immersed in a temperature controlled waterbath in such a way that the tissue was in contact with the water through the window. The water temperature was 37° C. The beam was aimed at the desired depth in to the heart. The sonication was performed and the transducer moved 5 mm before the next sonication. This was repeated five times in each row. Experiments with both frequencies, different pressure amplitudes, burst durations, and numbers and repetition frequencies were performed. After the sonications the tissue was cut along the sonicated line and the dimensions of the created cavities were measured. This was repeated in several rows in each heart.

Multiple sonications were repeated at different depths with the interval equal to the length of a single cavity. The sonications were performed in the order of their depth in tissue such that first sonication was aimed to the endocardium wall and the last to the epicardium. After the experiments were completed the hearts were fixed in formaldehyde.

Figure 2A:
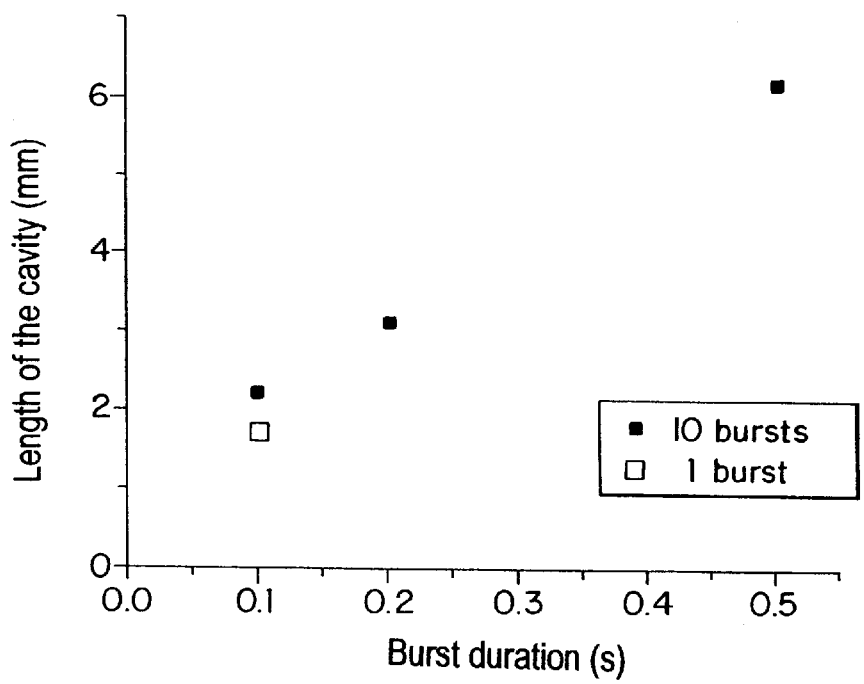
FIG. 2a is graph showing the burst duration on the x-axis and length of the cavity formed on the y-axis for a first set of values.
Figure 2B:
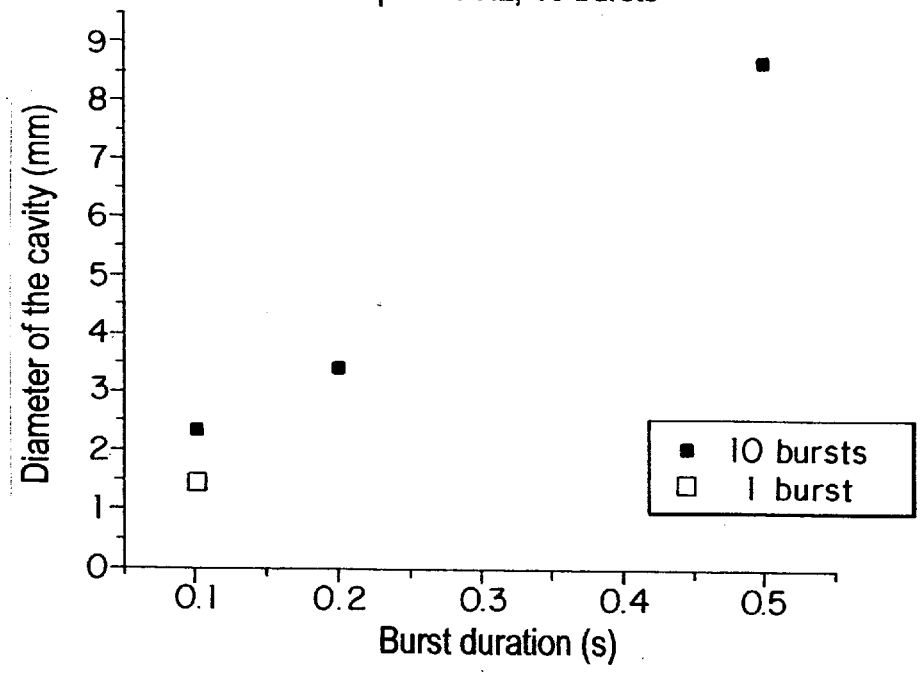
FIG. 2b is a graph showing the burst duration on the x-axis and the diameter of the cavity formed on the y-axis for a first set of values.
Figure 2C:
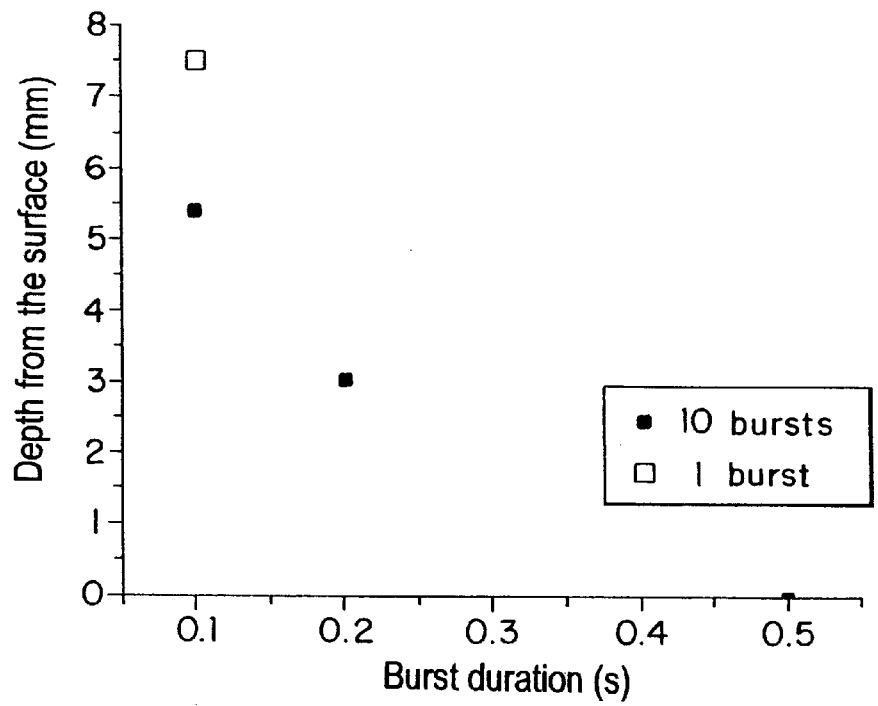
FIG. 2c is a graph showing the burst duration on the x-axis and the depth from the surface of the cavity formed on the y-axis for a first set of values.

Many of the high amplitude burst sonications at 2.02 MHz disintegrated the cardiac tissue leaving a cavity in the tissue. FIG. 1 shows a photograph of some of these cavities. The size, location, and to some extent the shape of the cavity was dependent on the sonication parameters. FIGS. 2a, 2b, and 2c show the effects of the burst duration on the length and diameter of the cavity and its depth from the epicardium. Both the width and length of the cavity increased as a function of burst duration however, the distance from the surface reduced as the burst duration increased. This means that the cavity is forming in front of the focal spot at the longer burst durations. Thus, shorter sonications are required to generate the cavities at the focal depth.

Figure 3:
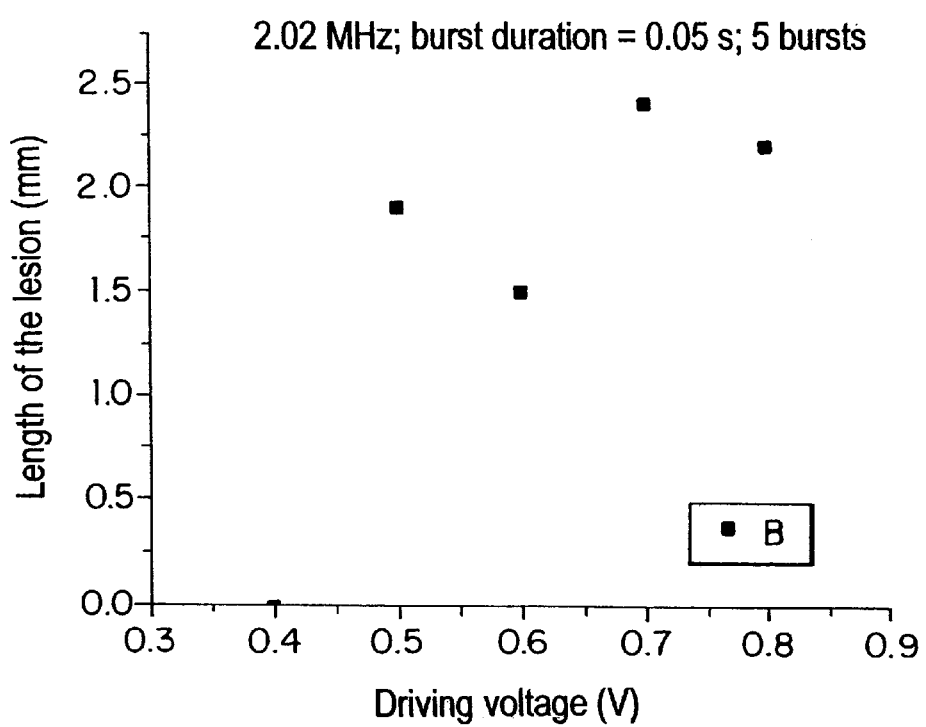
FIG. 3 is a graph showing the driving voltage on the x-axis and length of the cavity formed on the y-axis.

FIG. 3 shows that the cavity length is not strongly driving voltage (intensity) dependent above a threshold value that forms the cavity. This is with relatively short sonications and pulse repetition frequency of 1 Hz.

Figure 4A:
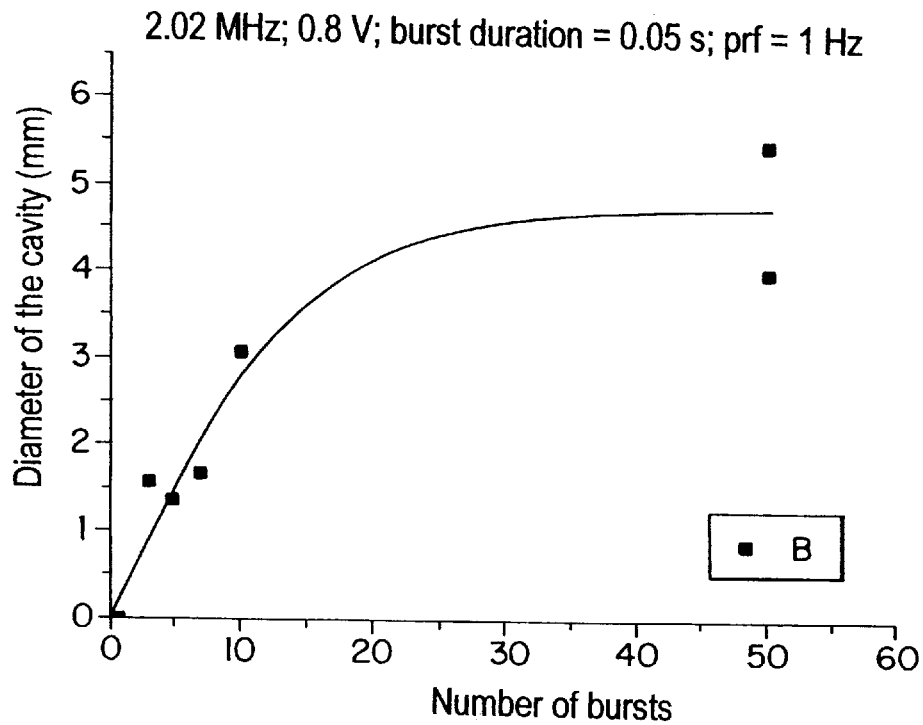
FIG. 4a is a graph showing the number of bursts on the x-axis and diameter of the cavity formed on the y-axis.
Figure 4B:
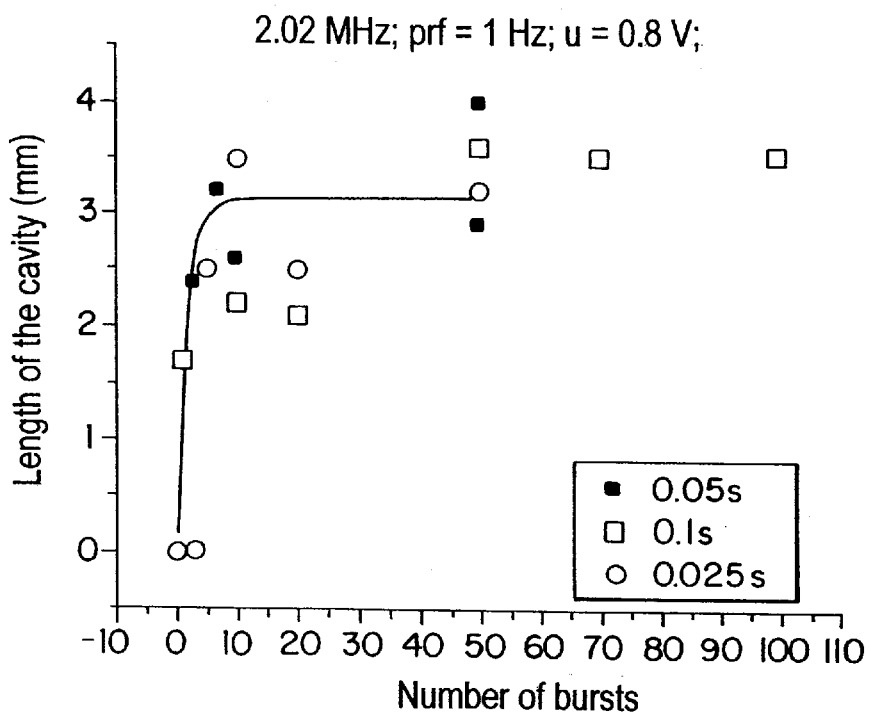
FIG. 4b is a graph showing the number of bursts on the x-axis and length of the cavity formed on the y-axis.

At the short burst length the number of bursts does not have a strong influence on the cavity length or its diameter after about 5 bursts of 0.05 s in length repeated at 1 Hz rate as shown in FIGS. 4a. And 4b.

Figure 5A:
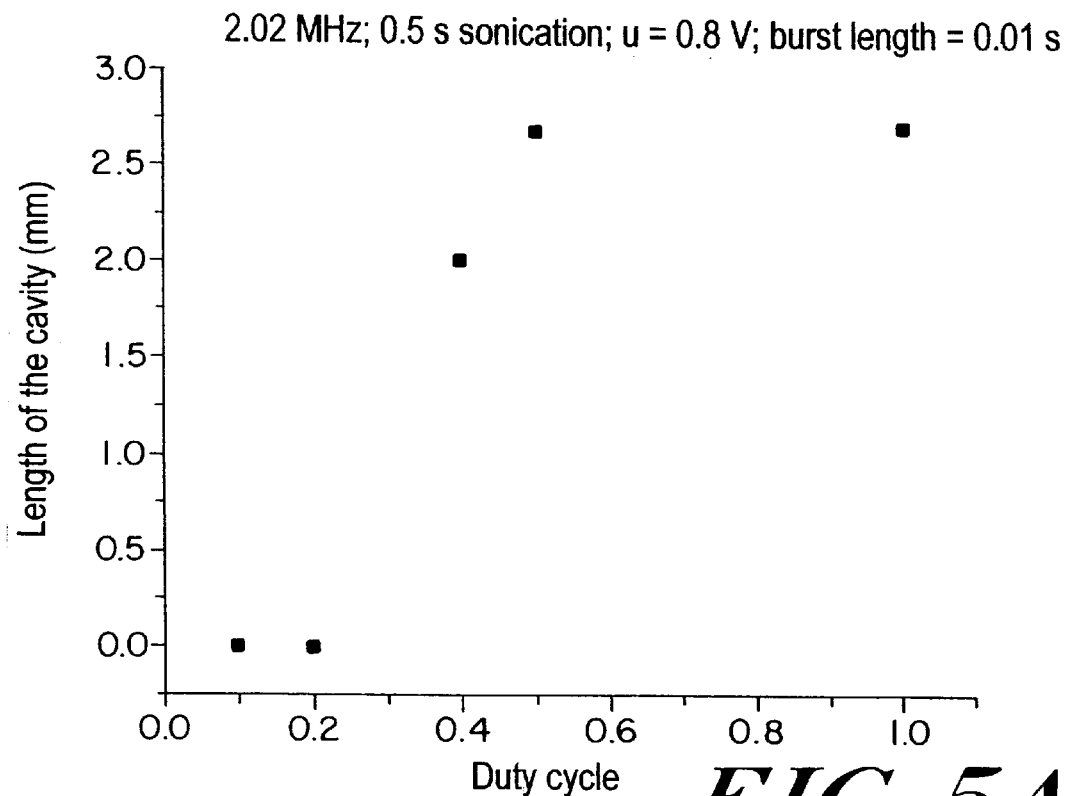
FIG. 5a is a graph showing the duty cycle on the x-axis and length of the cavity formed on the y-axis for a second set of values.
Figure 5B:
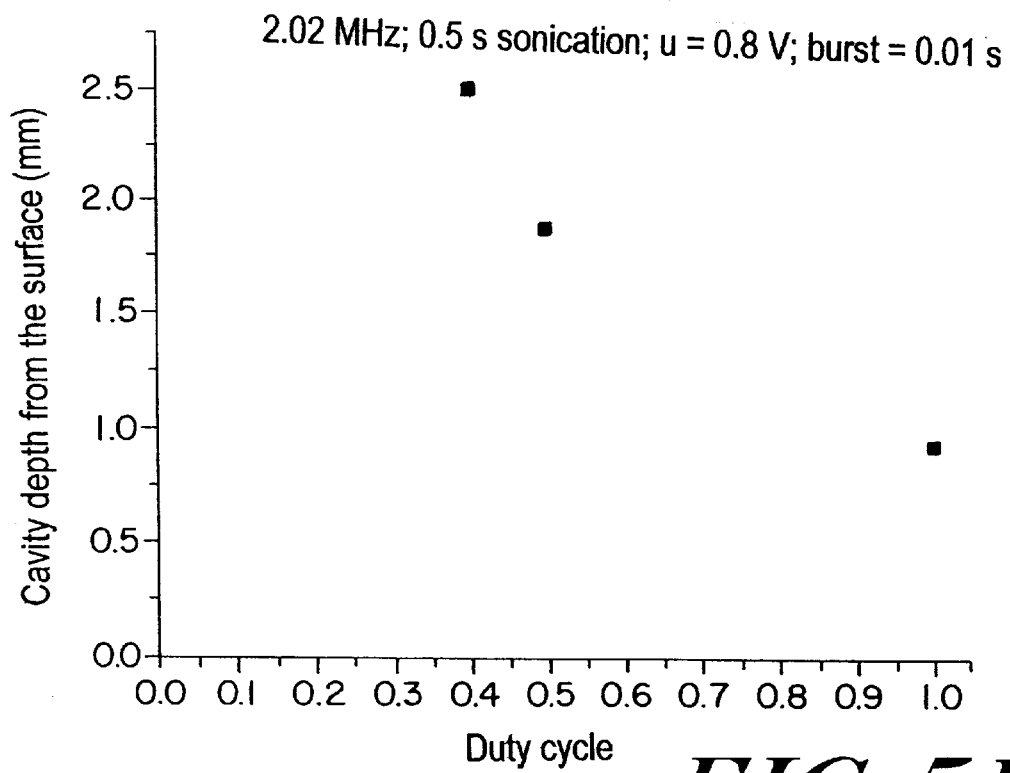
FIG. 5b is a graph showing the duty cycle on the x-axis and depth from the surface of the cavity formed on the y-axis for a second set of values.
Figure 6A:
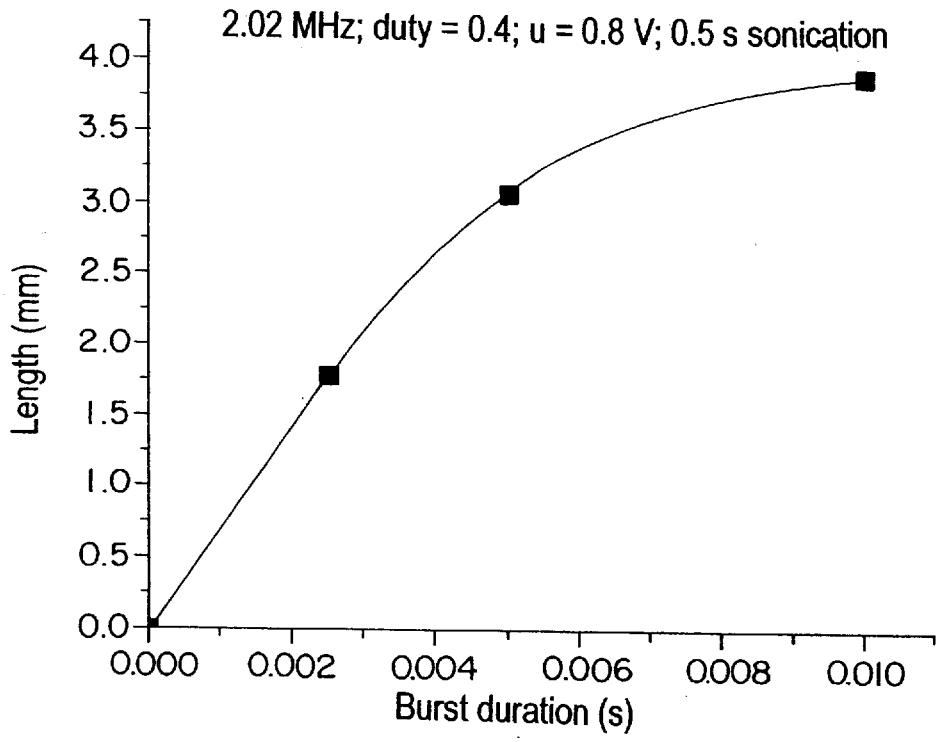
FIG. 6a is a graph showing the burst duration on the x-axis and length of the cavity formed on the y-axis for a third set of values.
Figure 6B:
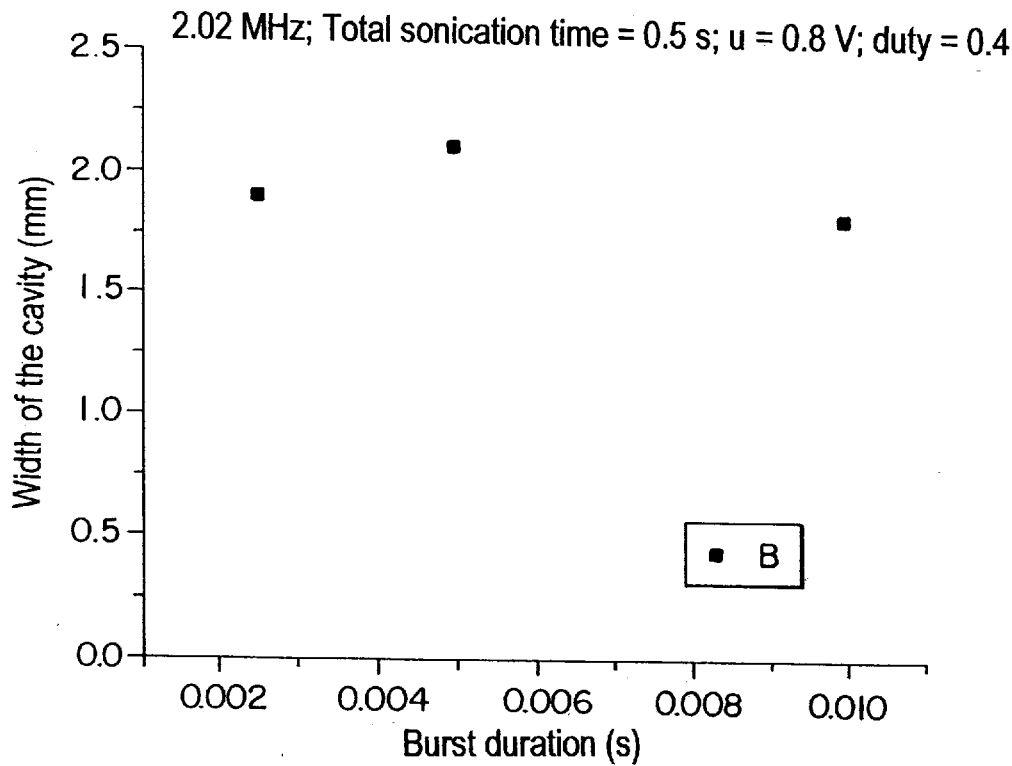
FIG. 6b is a graph showing the burst duration on the x-axis and the width of the cavity formed on the y-axis for a third set of values.

Finally, the total sonication time was fixed to 0.5 s and then different sonication parameters were tested. First, the burst length was fixed to 0.01 s and the duty cycle varied. FIGS. 5a and 5b show that the lower duty cycles did not produce any cavity until at 0.4 the cavity was formed. The length was about the same as with the higher duty cycles. However, the depth of the cavity from the epicardium reduced as the duty cycle increased. Thus, the duty cycle of 0.4 was selected for the next study that evaluated the influence of the burst duration during the 0.5 s sonications. FIGS. 6a and 6b a show the length of the lesion to increase up to 0.005 s and then increase only slightly at 0.01 s. The width of the cavity was insensitive to the burst duration under these conditions.

The lower frequency of 0.5 MHz did not produce cavities at the maximum power output level until continuous wave sonication for 0.5 s was used. The resulting tissue damage was larger, and the tissue was full of small holes but there was not a complete cavity. The shorter burst sonications did not produce observable tissue damage.

Figure 7:
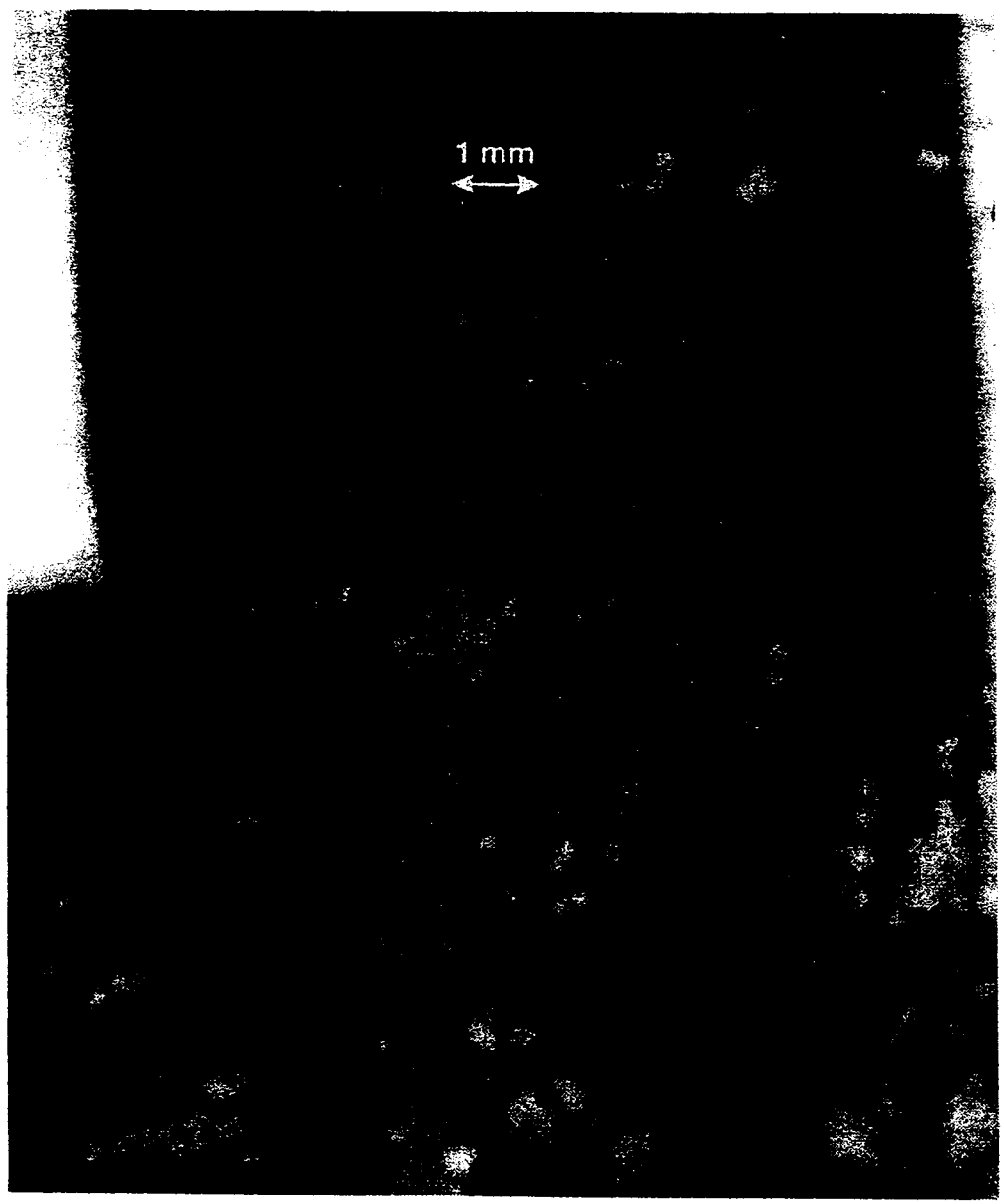
FIG. 7 is a photograph of multiple sonications that induced cavities through the cardiac wall.

Several sonications with parameters that produced cavities in the previous sonications were selected. These were all performed at the frequency of 2 MHz. These sonications showed that channels through the ventricular wall could be induced as shown in FIG. 7.

The experiments have demonstrated for the first time that ultrasound can be used to generate channels through the ventricular wall. These cavities may offer an alternative to laser induced cavities. It has been also shown that the cavities can be induced deep in the ventricular wall without direct contact of the applicator to the lesion site, allowing different channel geometries to be investigated to optimize the perfusion effects. For example cavities that do not come all the way through the endocardium can be easily formed. These cavities may also prove to be useful for destroying conduction pathways that cause arrhythmia.

The transducers used here were designed for high power ultrasound experiments and were not optimized for the cardiac sonications. In these experiments a spherically curved transducer was used to focus the beam, however, lenses or phased arrays can also be used for the task. Smaller transducers positioned manually by the surgeon on the epicardium when the heart is exposed can be easily designed and constructed. Transducer geometry to allow the applicator to be positioned via an incision between the ribs is also feasible. Similarly, catheter based applicators delivered onto the heart via blood vessels could be constructed.

Figure 8:
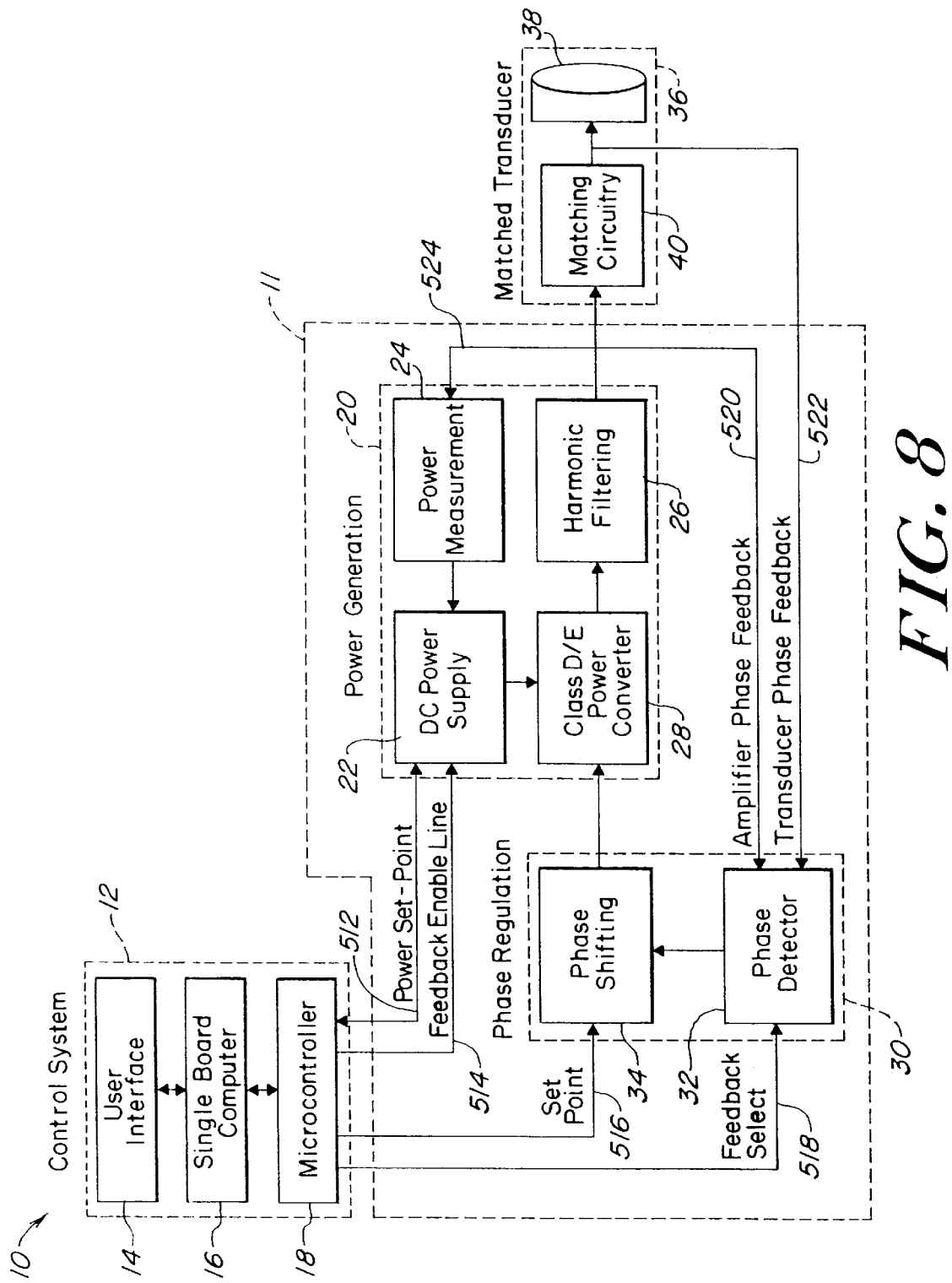
FIG. 8 is a block diagram showing the phased array ultrasound driving system.

The ultrasound phased array system 10 is shown generally in FIG. 8. The ultrasound phased array system 10 generally comprises a control system 12, controlling a plurality of channel driving systems 11, that each provide power to a corresponding matched ultrasonic transducer 36. The channel driving system 11 comprises a power generation system 20 and a phase regulation system 30. The control system 12 provides a power set point input 512 and a feedback enable signal 514 to the power generation system 20 and a phase set point input 516 and feedback select signal 518 to the phase regulation system 30. The power generation system 20 provides an output driving signal to the matched transducer 36 and includes a power feedback input 524. The phase regulation system 30 includes an amplifier phase feedback signal 520 from the immediate output of the power generation system 20 or alternatively a transducer phase feedback signal 522 after the matching circuitry at the matched transducer input 36 to provide phase correction to the power generation system 20.

As will be appreciated by one skilled in the art, each matched transducer 36 is a single array element of the ultrasonic phased array 10 and must be individually controlled in both power and phase in order to produce a desired wave form. This is necessary to create acoustic fields of constructive and destructive interference for a variety of phased array shapes and sizes. It is also critical to have individual control of power and phase of array elements in arrays whose elements have various surface area geometries, or to drive an array with non uniform power intensities for each of its elements in order to achieve a desired result. Each matched transducer 36 is driven by a separate power generation system 20 and phase regulation system 30. One of ordinary skill in the art will recognize that a plurality of ultrasonic transducers, each controlled by a separate power generator system 20, and phase regulator system 30, comprise the ultrasonic phased array system 10. It will be appreciated by one of skill in the art that the phased array may be of any desired orientation and geometry. The problem of various geometries in calculating the appropriate phase and power is a problem well known in the art.

In order for the ultrasound phased array system 10 to create an acoustic focus capable of vaporizing tissue the system must be able to control the power and phase of the ultrasonic energy emanated from each ultrasonic transducer. The control system 12 includes: a user interface 14, which allows the operator to input user commands; a single board computer 16 for receiving and interpreting commands from the user interface 14 to communicate with the system's microcontroller 18. The microcontroller 18 determines the power set point input 512 for the power generation system 20, the phase set point input 516 for the phase regulation system 30, and enables the feedback enable signal 514 of both the power generation system 20 and the feedback select signal 518 of the phase regulation system 30.

In one embodiment, the power conversion system 20 comprises a switching DC power regulator 22, a power measurement system 24, a Class D/E power converter 28, and a harmonic filtering system 26. The DC power regulator 22 provides a regulated DC power to the class D/E power converter 28. The power measurement system 24 samples the output of the harmonic filtering system 26 and provides feedback to the DC power regulator 22, which will regulate the DC power available to the Class D/E power converter to the level set by the power set point control signal 512.

The Class D/E power converter 28 converts the DC power provided by the DC power regulator 22 to a high power, high frequency square wave. In the preferred embodiment a frequency between 0.5 and 10 MHz and more particularly, between 1.5 and 4 is optimal for vaporization of cardiac tissue. The DC power regulator 22 consists of a DC-to-DC down converter which regulates the DC voltage from 0 V to a constant voltage for the Class D/E stage 28. Harmonic filtering 26 receives the high frequency signal from the Class D/E power converter 28 and further filters the signal to produce a sinusoidal output signal. This sinusoidal output signal is sampled by the power measurement system 24 to provide a feedback input to the DC power supply 22, to adjust the power output supplied to the Class D/E power converter 28, based on the set point provided by the microcontroller.

The phase regulation system 30 comprises a phase shifter 34 and a phase detector 32. The phase shifter 34 receives a phase set point 516 from the controller 12 and determines the timing of the switching input control signal 577 to the power generation system 20. The phase detector 32 will detect the phase of the feedback signal which is either the amplifier phase feedback signal 520 or the transducer feedback signal 522. This provides a closed loop feedback control of the phase of the output signal in order to account for imperfections in the system of the ultrasonic transducer element.

The output from the harmonic filtering system 26 is provided to a matching circuitry 40, which drives an ultrasonic transducer 38. Each matched transducer 36 is associated with matching circuitry 40 to provide an impedance match between the harmonic filter system 26 and the ultrasonic transducer 38. The impedance matching circuitry 40 is preferably adjusted so that maximum power transfer occurs between the driver system 11 and the ultrasonic transducer 38.

Figure 9:
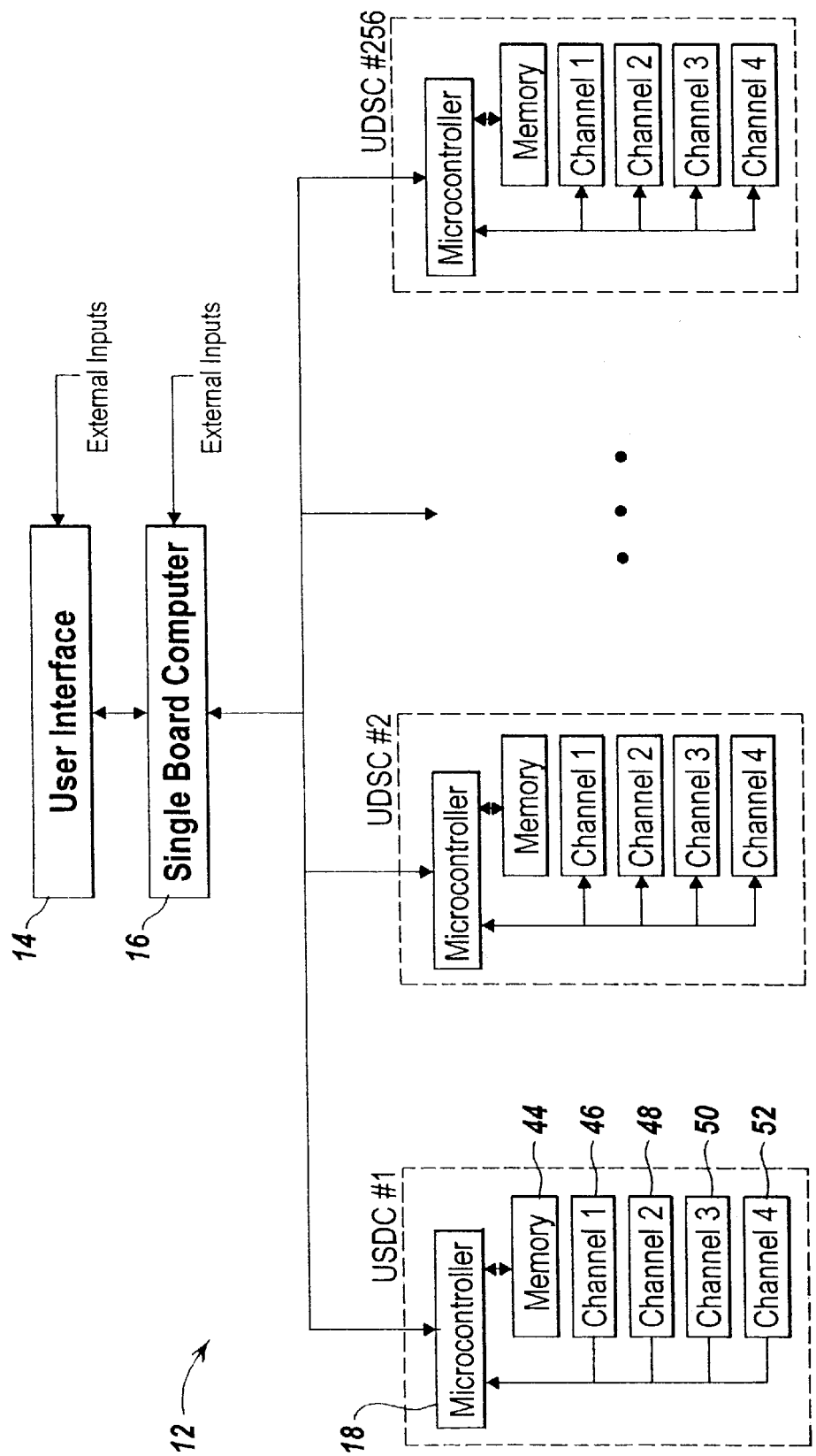
FIG. 9 is a block diagram showing the control architecture of the phased array driving system.

The control system 12 is shown in more detail in FIG. 9. In one embodiment, the amplifier system comprises up to 256 ultrasonic driving system cards (UDSC). Each card is capable of driving up to four individual channels with each channel corresponding to one matched ultrasonic transducer 36. Thus, in one embodiment of the ultrasonic array system 10, there can be up to 1,024 matched transducer elements 36 in the phased array. Each individual UDSC includes a microcontroller 42 which has a two separate read/write local memory banks 44: one for protected program storage and one for data storage. Each UDSC drives up to four single channel driving systems 11. The microcontroller 42 in the present invention is a Motorola 68HC11 microcontroller. In one embodiment the microcontrollers 42 interface with a single board computer 16 over a single data bus. The single board computer 16 is an Intel 486 based single board computer or equivalent. The single board computer 16 reports operational status to, and receives operational commands from, the user interface 14. It would be known to one skilled in the art that the user interface 14 may be operated manually by a human or operated automatically simultaneously with other devices such as a magnetic resonance imager or positioning system.

In the present embodiment, the user interface 14 inputs data regarding the desired acoustic focus point and calculates the appropriate power and phase for each individual driving system 11 and matched transducer 36 combination in order to achieve the desired acoustic focus point to create vaporization of the target tissue volume. These calculations are conventional and are well known in the art. The user interface 14 transmits the calculated power and phase data to the single board computer 16, that transmits the phase and power data to the appropriate USDC 12. The USDC 12 then drives each individual driving system 11 and matched transducer 36 combination to the desired phase and power output.

If it is necessary for the phase and/or power to be changed rapidly during a sonication, e.g. to scan the acoustic focal point of the array, or to create a rapid progression of acoustic focal points, the phase and power data can be downloaded directly to the UDSC's local memory 44 prior to the sonication. The local memory 44 stores the power and phase data for each channel. The single board computer 16 sequences the operation of the microcontroller 18 by directing the microcontroller 18 to execute the stored data.

In one embodiment of the ultrasound phased array system 10, the power and phase data is stored in a memory stack located within the microcontroller's data memory. This sequence of phase and power data comprises a software implementation of a random-access-memory data list, referred to in this implementation as the control stack. This allows the process to read the data, by retrieving the data from the stack while only keeping track of the stack locations. Preferably once the single board computer directs the microcontrollers that they will be processing stack information, the microcontrollers process subsequent stack data at the direction of a parallel line controlled by the single board computer 16. This has the advantage of dramatically reducing the communication overhead during sonication, which in turn allows the microcontrollers to more closely monitor the amplifiers while rapidly changing phase and power distribution patterns.

Figure 10:
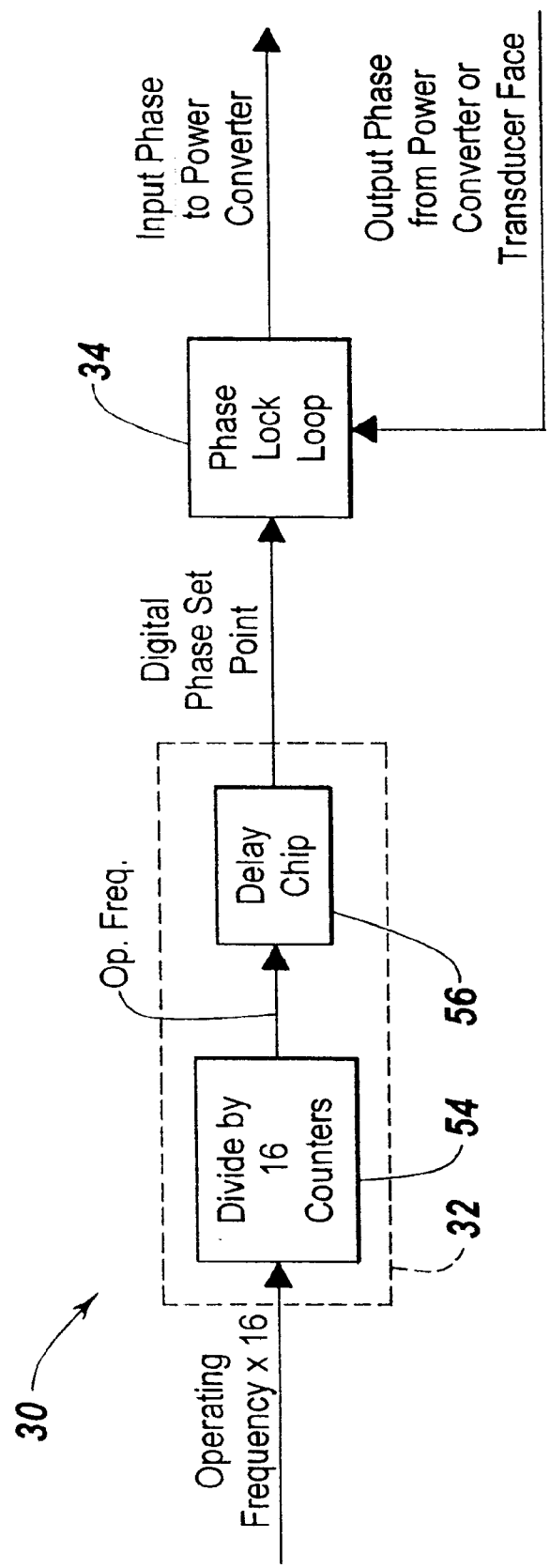
FIG. 10 is a block diagram showing the phase regulation system.

The phase regulation system 30 is shown in greater detail in FIG. 10. In one embodiment of the ultrasound phased array system 10 the phase regulation is a combination of both digital counters and delay circuitry. The input master clock operates at 16 times the frequency of the transducer (i.e. 48 MHz for a 3.0 MHz transducer), this input frequency is then provided to a programmable 4-bit divide-by-16 counter 54 which produces 22.5 degrees of frequency independent phase resolution and provides the operating frequency to the delay elements. In a preferred embodiment of the ultrasound phased array system, the finer resolution is provided by an 8-bit programmable delay chip 56 with 0.5 nanosecond resolution. This circuitry provides the ability to create higher degrees of phase resolution. In one embodiment of the ultrasound phased array system, 8 bits are used to control the phase. The first four bits are used to provide the 22.5 degrees of phase resolution using the programmable 4-bit counter 54. This combination of counters and delay circuitry is effective because it provides increased phase resolution while avoiding ultra high frequency master clock signals and a significant increase in chip count.

As will be discussed in greater detail below, the power generation system 20 implements a switching DC power regulator 22 which provides power to a DC to RF power converter. In the one embodiment of the ultrasound phased array system, a class D/E amplifier is used as the DC to RF power converter. This is also known to those skilled in the art as a sub-optimal Class E amplifier. The Class D/E switching amplifiers are based on the principle of using active switching devices, typically FETs, to drive a harmonic filter such that there is little to no power dissipation in the active switching device. In the preferred embodiment of the ultrasound phased array system the harmonic filter 26 is a low pass filter designed to attenuate the high harmonic components inherent in a switching design. The harmonic filter 26 has a desired cutoff frequency such that the second and third harmonics of the lowest operating frequency would not be significantly transmitted to the matched transducer 36.

The matching circuitry 40 provides impedance matching between the output of the driving system 11 and the ultrasonic transducer 38. Impedance matching maximizes the power transfer between the driving system 11 and the transducer 38 and allows for accurate power measurement. In the preferred embodiment of the ultrasound phased array system 10, the matching circuitry 40 is also capable of matching different impedances to ensure that the same range of power will be delivered to each individual element in the transducer array.

Figure 11:
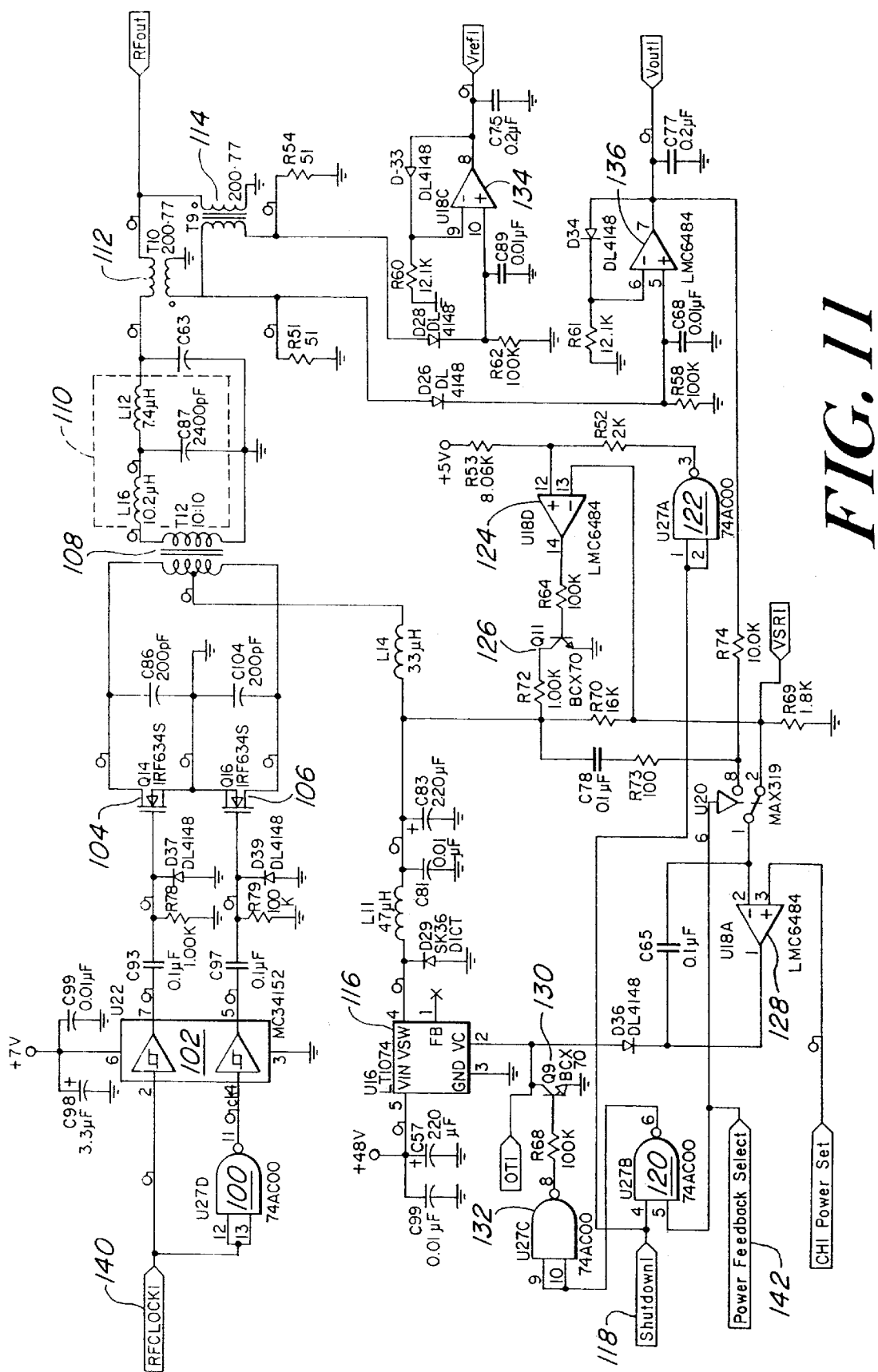
FIG. 11 is a schematic diagram showing a single driver element for an ultrasound channel in the phased array ultrasonic system.

A schematic diagram of a representative amplifier stage channel is shown in FIG. 11. The RF clock input 140 and its inverse, created by the inverter 100, are inputs to a signal conditioning amplifier driver 102, which provides signal conditioning in the form of providing a square wave output. The square wave outputs from the amplifier driver 102, which are 180° out of phase with each other, are provided to the inputs of transistors 104 and 106. Transistors 104 and 106 are preferably power switching MOSFETs and in one embodiment of the present invention are N-channel devices. The output of these devices are connected to opposite terminals of the primary side of transformer 108 which has a center tap connected to the DC switching power regulator 116. The secondary of transformer 108 is connected to a harmonic filtering system 110 whose purpose is to attenuate the high harmonic components inherent in a switching power supply design. In order to correctly measure and regulate power in the amplifier stage, a dual directional coupler consisting of transformer 112 and 114 provides two output signals representing the forward and reflected power delivered to the load. The forward power from transformer 112 is provided to op amp 136 which provides the forward voltage signal Vforl, and the reflected power is provided from transformer 114 to op amp 134 which provides the reflected voltage signal Vrefl.

The switching power supply regulator 116, which in the present embodiment is an LT1074, controls the power available to the switching transistors 104 and 106. The power regulator 116 receives an input voltage of 48 volts, which it then regulates to an output voltage between 0v and 48v. This output voltage which is supplied to the center tap of transformer 108 will determine the power available at the transducer 38. The output voltage is determined by the power set signal 141. If the power feedback select is enabled, the power set signal 141 is compared to Vfor 1, the forward voltage going to the transducer 38. If there is a difference between these voltages, an error signal from comparator 128 will adjust the output of the power regulator 116 appropriately.

The ability to provide power feedback is critical when utilizing a tuned amplifier such as Class D/E. Class D, Class E, or Class D/E amplifiers will suffer variations in power due to different transducer impedances off resonance. In the preferred embodiment, the power feedback system reduced variation in measured output power from 20% to less than 1%. This control is critical when using non-uniform array geometries, or if power control is critical for other applications.

Patient safety and equipment protection are preferably provided by the ability to shut down an amplifier stage if a failure occurs. Shut down of the amplifier stage channel is accomplished when the shut down signal 118 and power feedback select signal 142 are both high. This results in transistor 130 being driven into saturation and grounding the VC input of the switching power regulator 116 thus cutting off all power to the switching transistors 104 and 106. This could occur for instance if the measured reflected power from the dual power coupler, exceeded a threshold indicating a failure in the ultrasonic transducer element. In addition if an over temperature condition occurs signal OT 143, will go low, grounding the VC input to the power regulator 116 also cutting off power to the channel.

Figure 12A:
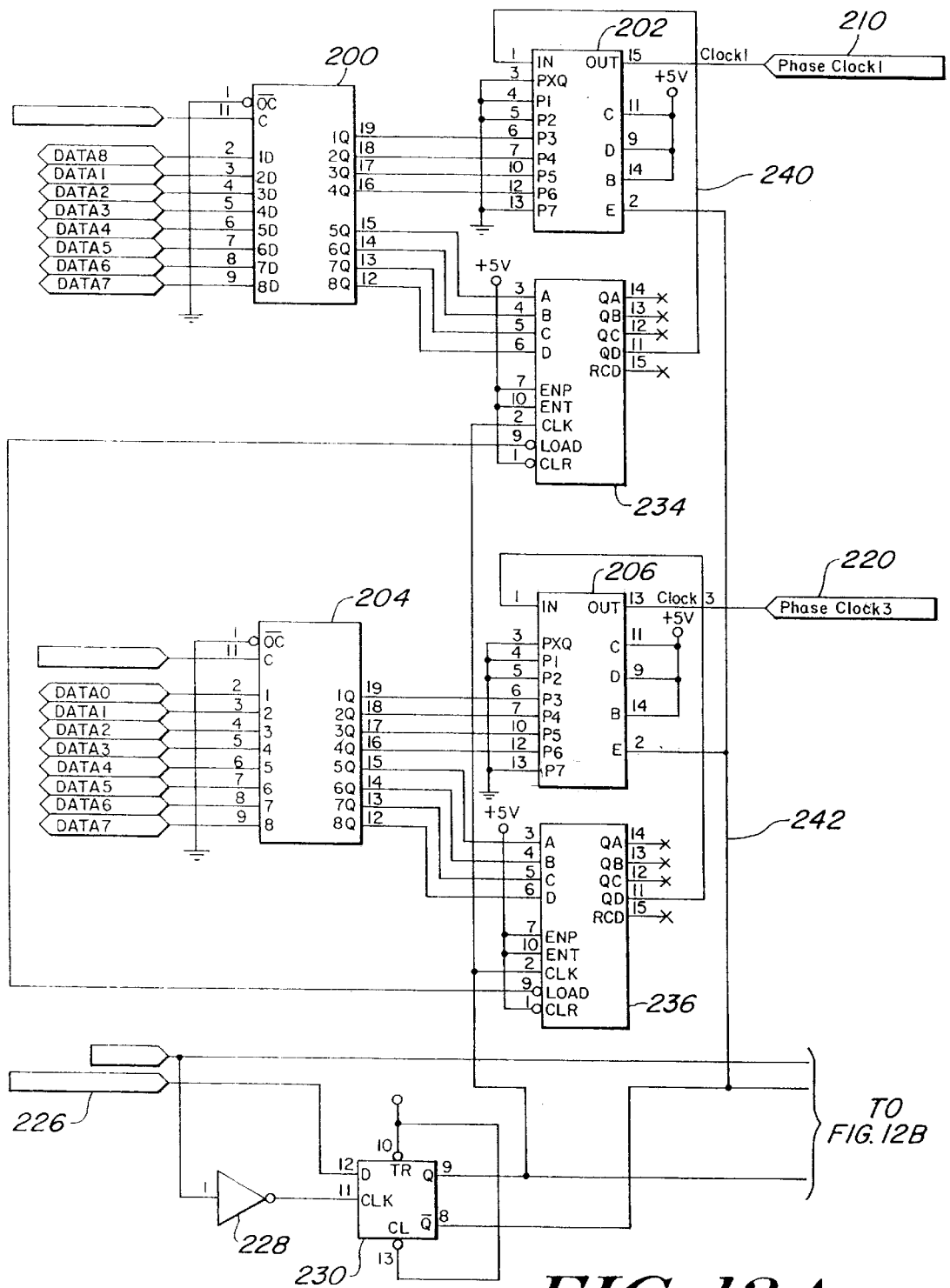
FIG. 12 is a schematic diagram showing the phase controller circuitry of the phased array ultrasonic system.
Figure 12B:
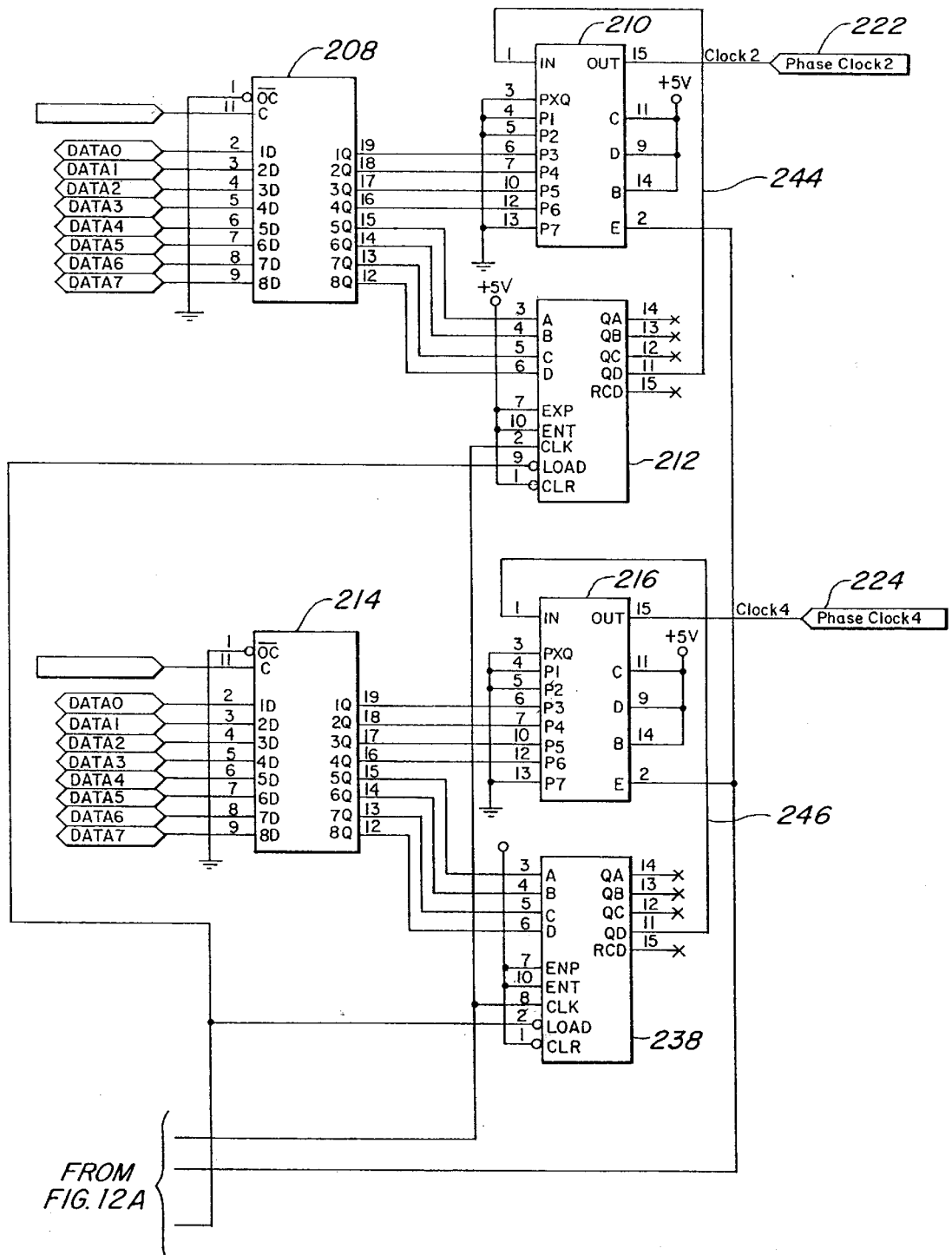

FIG. 12 is the schematic diagram for the digital phase shifter of the ultrasound phased array system 10. The digital phase shifter outputs, as shown in FIG. 12, are the phase clock inputs 218, 220, 222, 224 that drive the phase correction circuits in FIG. 13. The UDSC microcontroller provides eight bits of phase data to the inputs. Four bits of the data are provided to the four bit counters 234, 236, 238, and 240, and four bits of the data are provided to the digital delay chips 202, 206, 210, and 216. The 4-bit counters 234, 236, 238, and 240 provide the first four bits of phase information which, via lines 241, 242, 244, and 246, will turn on digital delay chips 202, 206, 210, and 216, which provide a second 4 bits of phase data, after the preset count of the 4-bit counters 234, 236, 238, and 240 is concluded. The 8-bit delay chip where bits 0, 1, and 7 are hardwired, resulting in 1.08 degrees of phase resolution at 1.5 MHz. The phase clock output 218, 220, 222, 224 is provided after both delay functions have been achieved. As can be seen in FIG. 12, there are four channels of digital phase shifters per circuit card, and in the preferred embodiment of the invention there would be one digital phase shifter for each channel of the ultrasound phased array system.

Figure 13A:
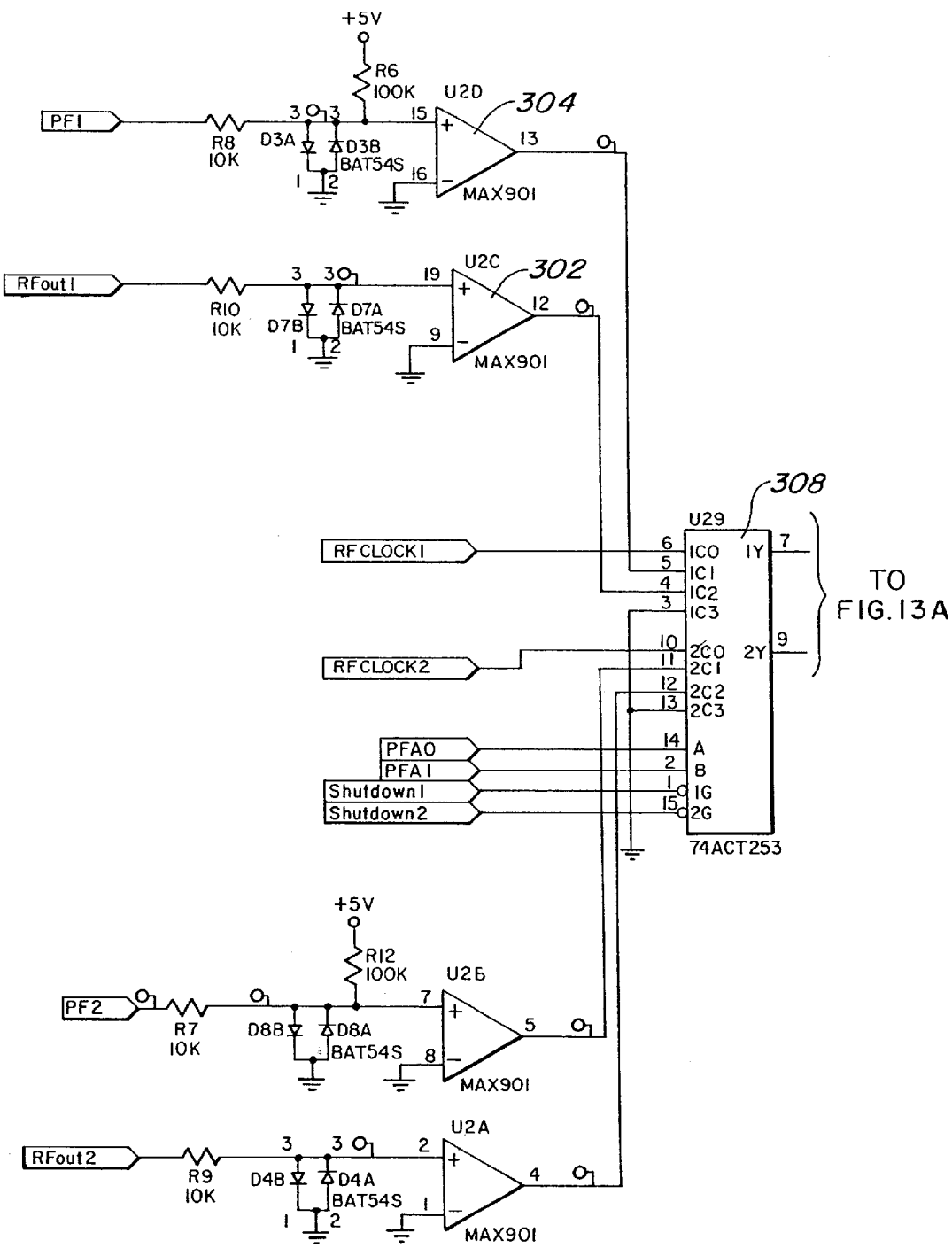
FIG. 13 is a schematic diagram showing the phase correction circuitry for the phased array ultrasonic system.
Figure 13B:
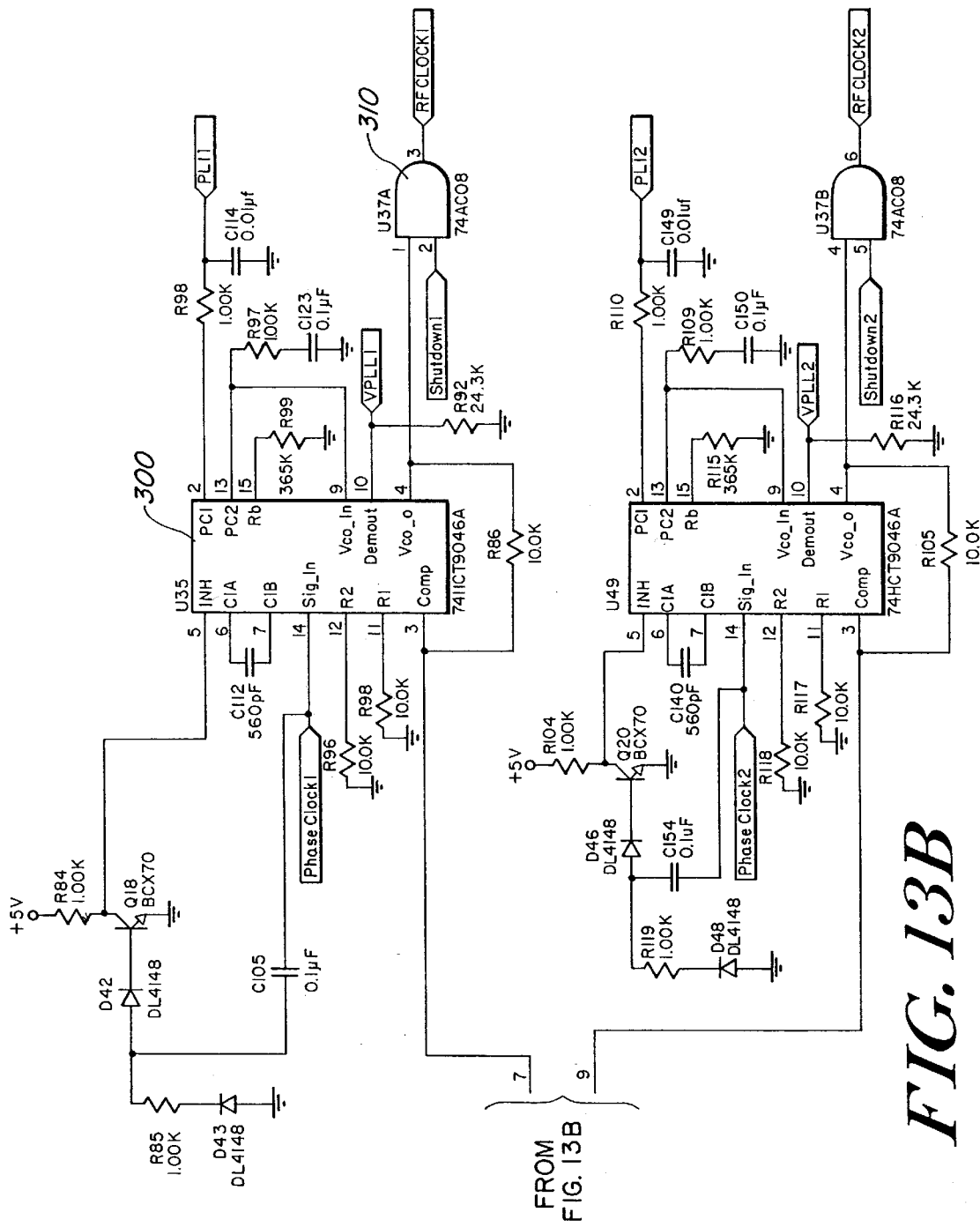

FIG. 13 is a schematic diagram of an embodiment of the automatic phase detection/correction circuitry for the ultrasound phased array system 10. The output signal 306 from the amplifier stage, $RF_{out}$, is provided to the phase locked loop 300 via the comparator 302 and multiplexer 308. The phase locked loop 300 will synchronize the $RF_{out}$ signal with the phase clock signal provided from the digital phase shifter. This output is provided to gate 310 such that if the shutdown signal input to 310 goes low there will be no driving signal for the amplifier and that channel will be effectively shut off. The output from the gate 310, RF clock, which drives the Class D/E amplifier shown in FIG. 11, is also fed back and is selected via multiplexer 308 in order to provide necessary feedback to ensure synchronization of the signals within phase locked loop 300. This will provide correction for the inherent non-linearities in the class D/E amplifier, as well as any aberrations caused by other sources.

The preferred embodiment of the phase regulation system 30 described above allows the non-linear Class D, Class E, or Class D/E amplifiers to be used. These amplifiers typically have almost 50% variation in phase depending upon the power output. By providing phase feedback at either the amplifier output or the transducer face this phase variation is reduced to less than 3%.

The preferred embodiment of phase regulator system 30 described above also advantageously increases the peak acoustic intensities at the acoustic focus point. There are several sources of phase errors within the embodiments described. The first is the matching network 40, which will cause a phase shift to occur between the amplifier output voltage and the transducer 38. A second source of phase error is created by transducer elements being different shapes or sizes. By providing phase feedback measurements from the transducer face, an increase of 25% in acoustic intensity at the acoustic focus is achieved over no phase feedback. In addition, phase feedback measurements from the amplifier output result in an 18% increase in acoustic intensity.

Figure 14A:
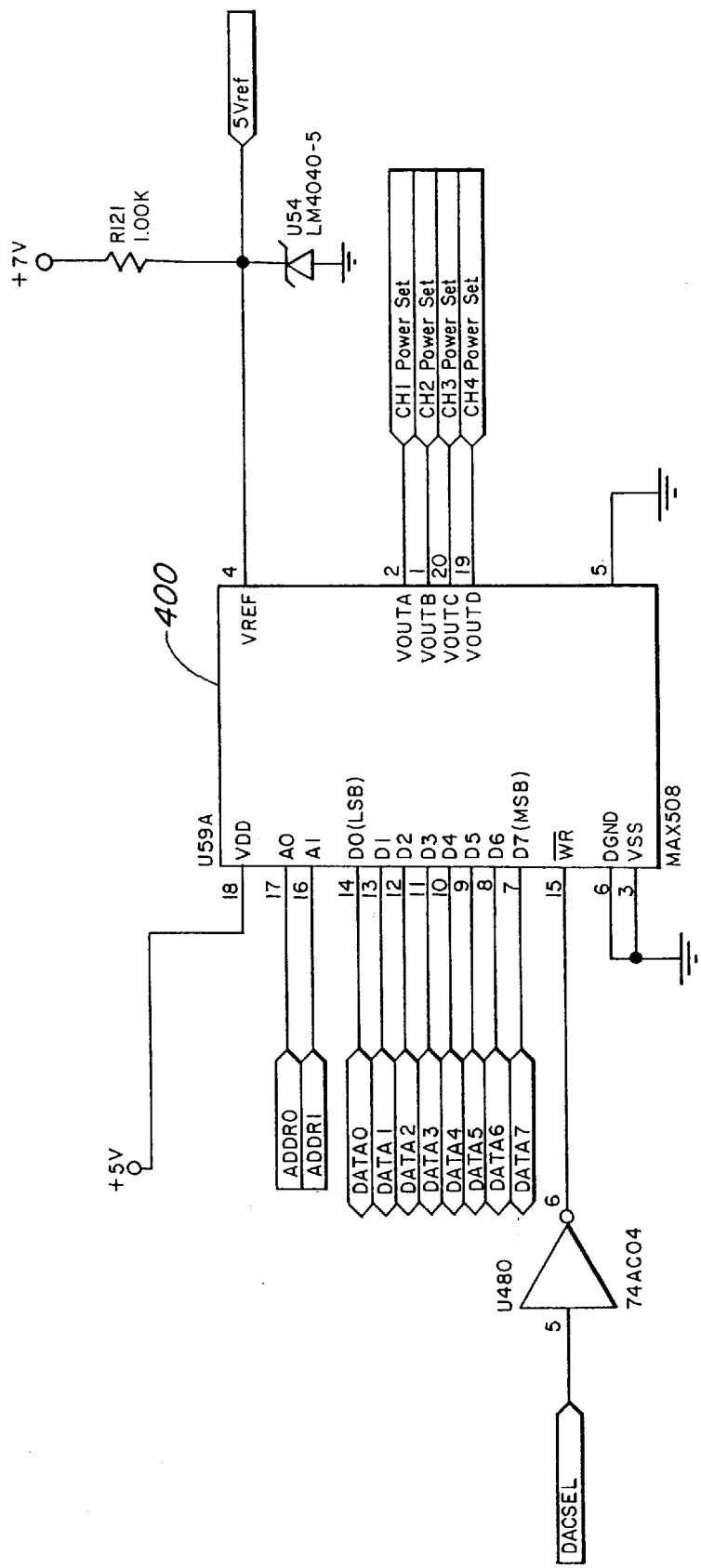
FIG. 14A is a schematic diagram showing the data acquisition digital to analog converter supplying the power set point to the driver element in the phased array ultrasonic system.
Figure 14B:
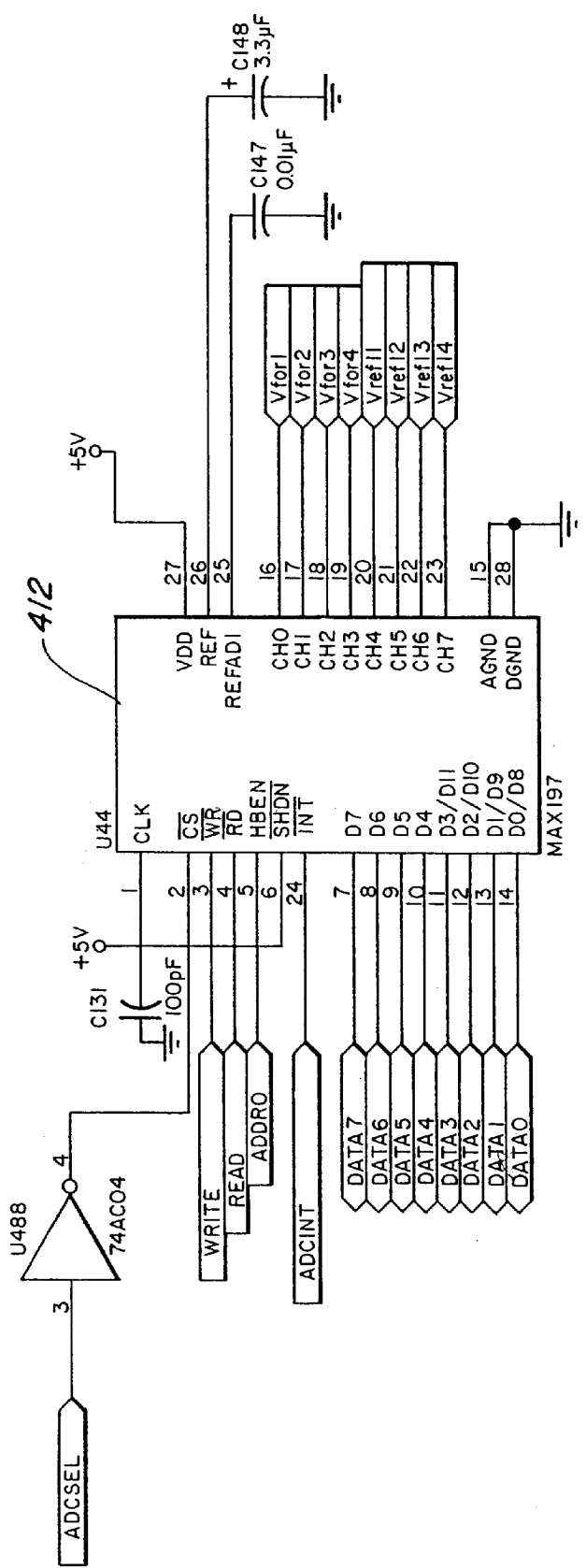
FIG. 14B shows the measurement system analog to digital converter for measuring the forward and reflected power in a phased array ultrasound system.
Figure 14C:
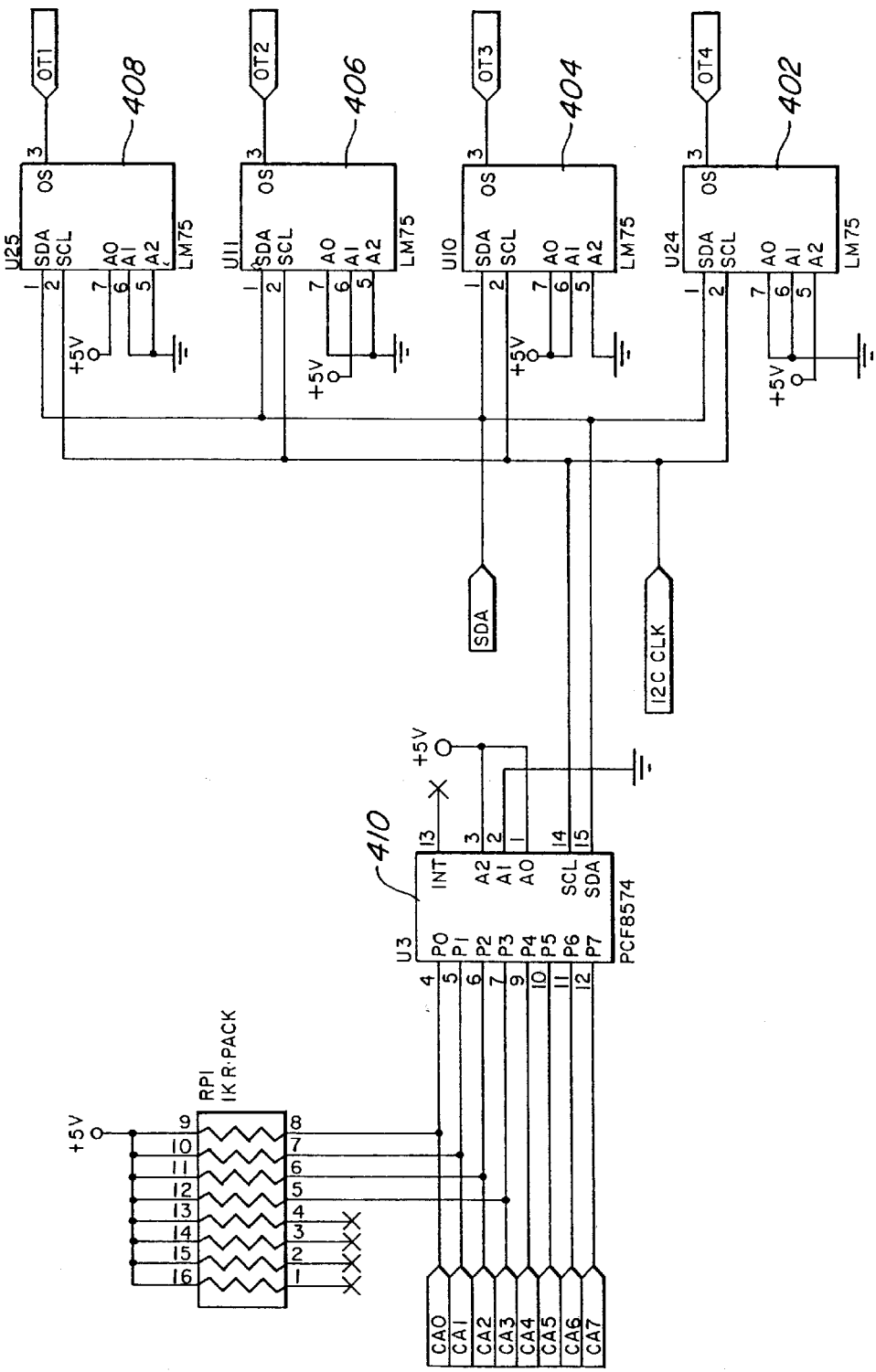
FIG. 14C is a temperature sensor for detecting elevated temperatures to protect circuitry for each driving channel of the ultrasound driving system.
Figure 15A:
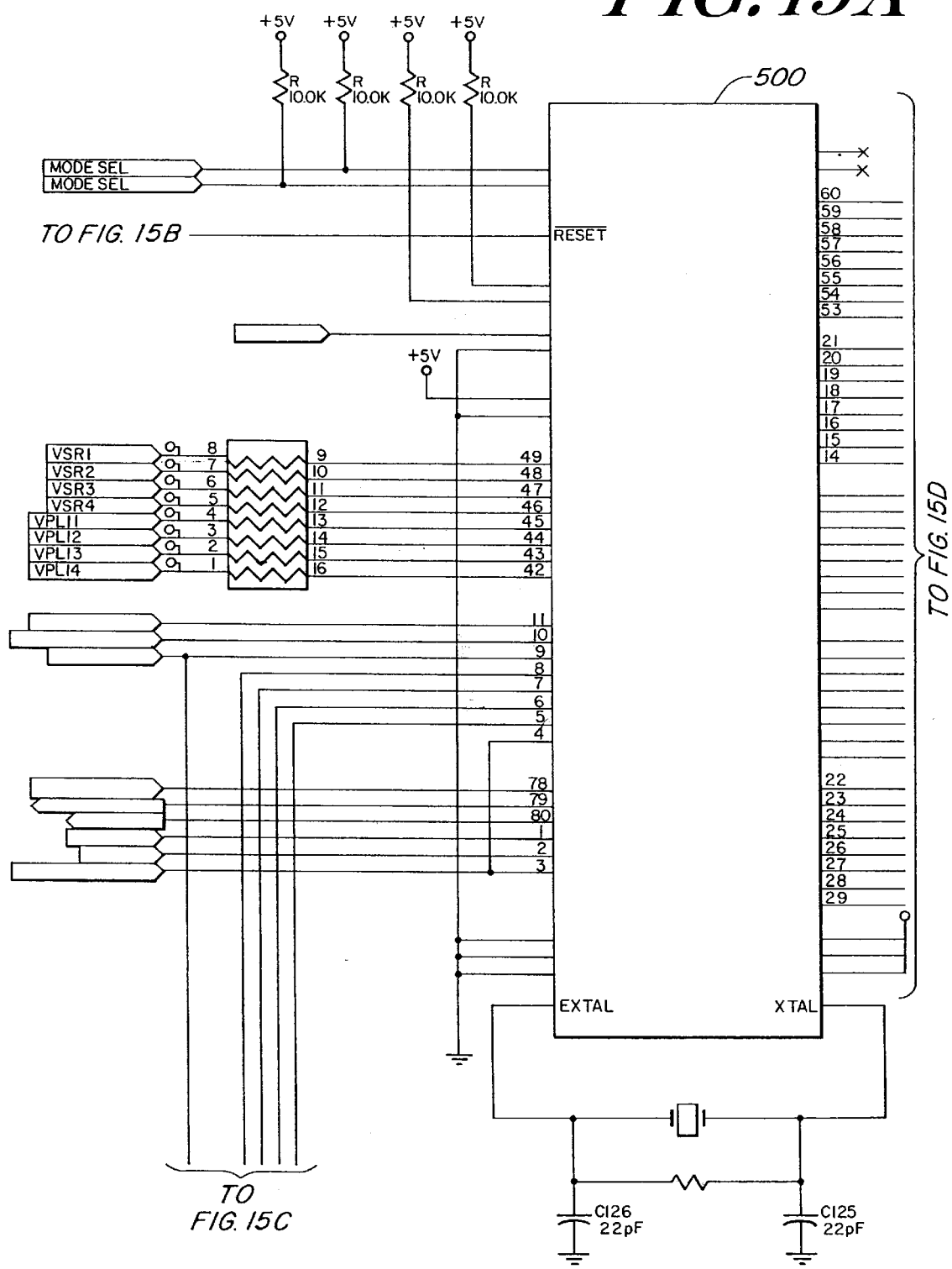
FIG. 15 is a schematic diagram showing the microcontroller and the circuitry associated with the microcontroller and memory.
Figure 15B:
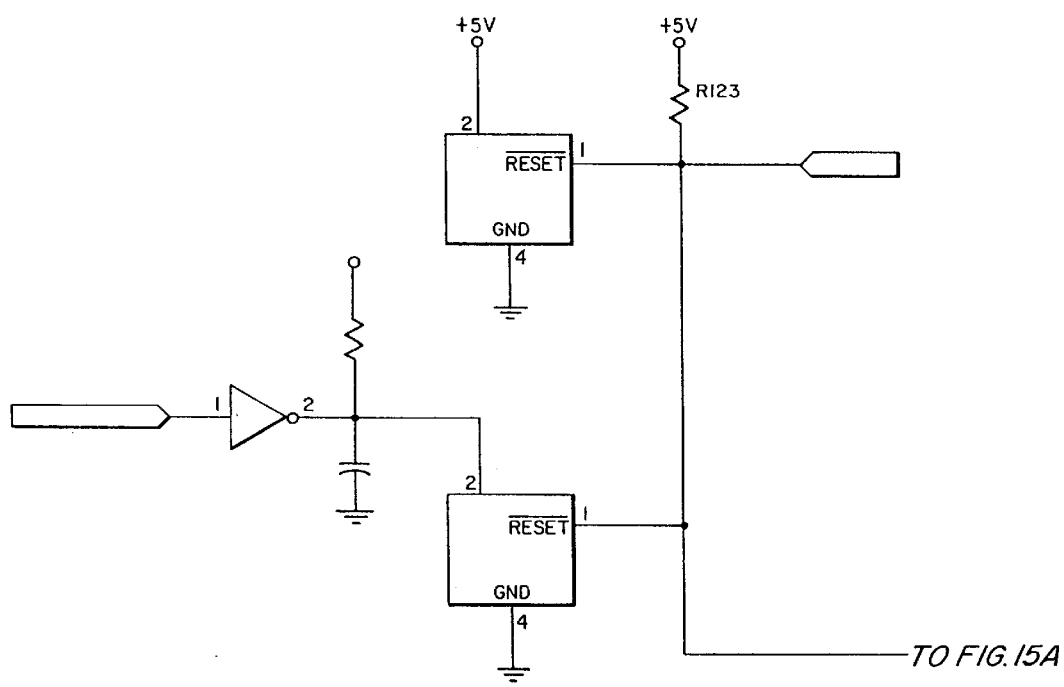
Figure 15C:
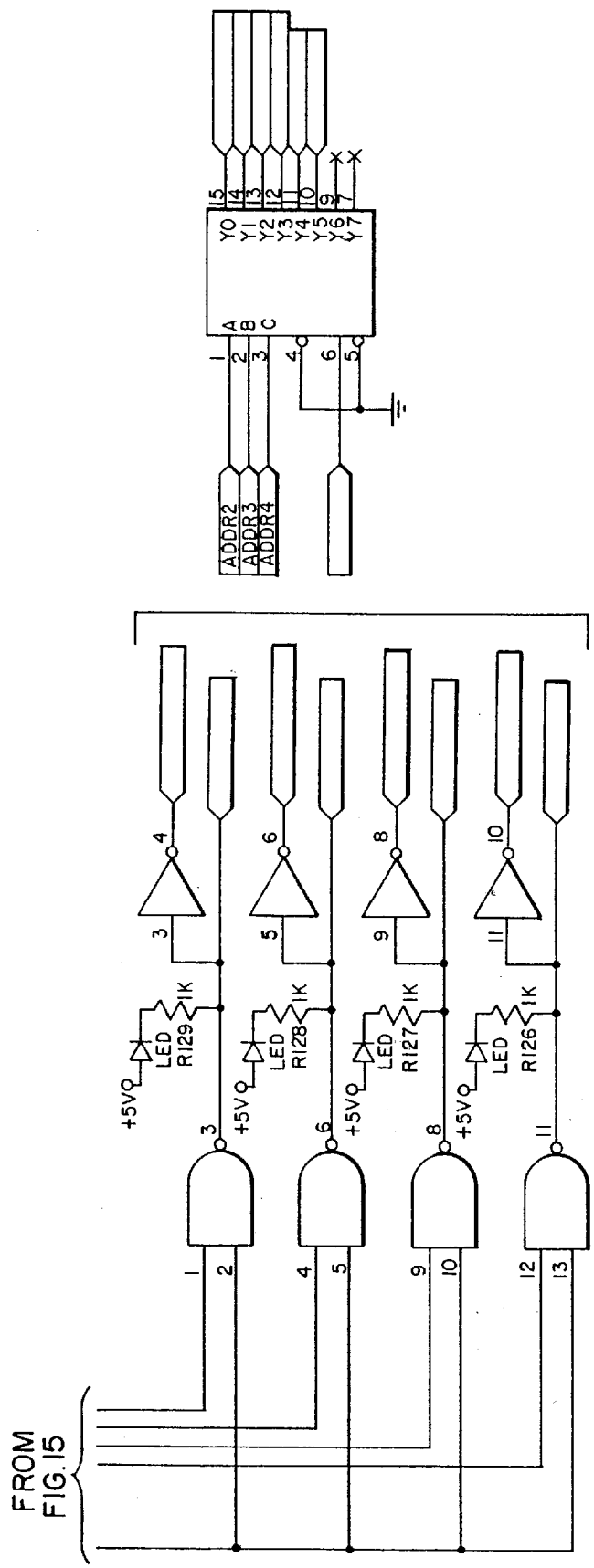
Figure 15D:
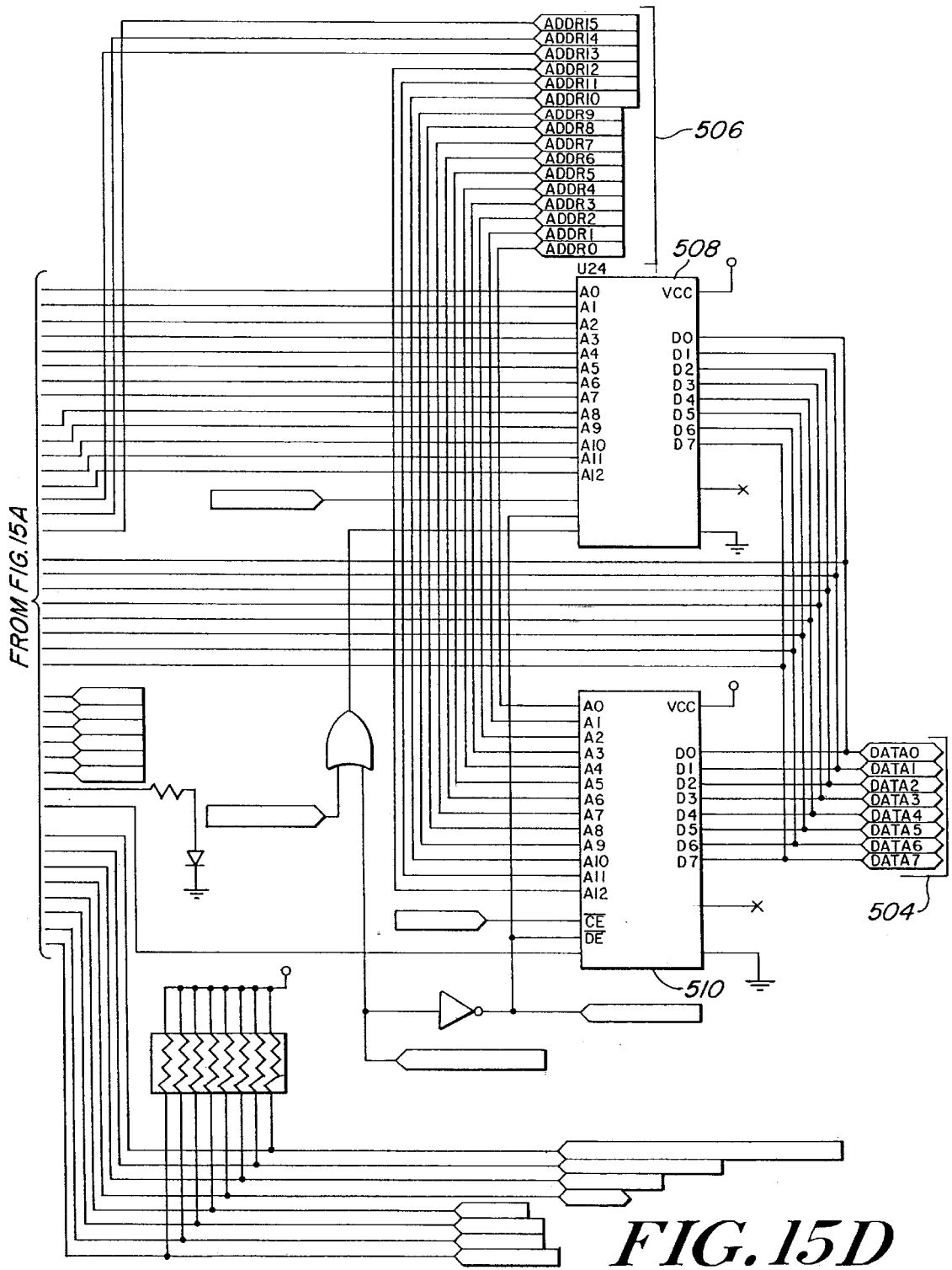

FIGS. 14A, 14B, and 14C provide the schematic diagrams for the data acquisition system of the ultrasound phased array system 10. In FIG. 14A, the digital to analog converter 400 accepts data lines, data 0 through data 7, and address lines ADDR0 and ADDR1 to produce the power set voltages for each of the channels used in the ultrasonic phased array. These outputs, CH Power set, are provided to the amplifier stage shown in FIG. 11 and provide the set point to the DC switching power regulator 116.

In FIG. 14B the analog to digital converter 412 accepts inputs of forward and reflected power from each of the channels in the ultrasonic phased array system and converts that analog data to digital data and stores that data in memory, where it is retrieved by the single-board computer 16.

In FIG. 14C, temperature sensors 402, 404, 406, 408 detect elevated temperatures to protect circuitry for each driving channel of the ultrasound driving system.

FIG. 15 is a schematic diagram of one embodiment of the microcontroller and its associated circuitry. Microcontroller 500 has associated with it memory 508, 510. The address lines 506 and data lines 504 provide the read/write address and data to be stored in the memory. In addition control signals are generated in the microcontroller 500, to control the phased array ultrasonic system electronic circuitry.

What is claimed is:

1. An ultrasonic system for selectively and non-invasively vaporizing body tissue, the system comprising:
    an extracorporeal array of ultrasonic transducers, each of said transducers being capable of producing an ultrasonic wave; and
    a plurality of channel driving systems, each of said channel driving systems being coupled to one of said transducers and providing an output signal having an amplitude and a phase to a corresponding one of said transducers, each of said channel driving systems including at least one of a power measurement system and a phase detector for providing measured values of a respective one of said amplitude and said phase of said output signal, each of said channel driving systems adjusting said corresponding output signal based on a pre-selected value of said output signal and the measured value of said output signal to selectively vaporize said body tissue.

2. The ultrasonic system of claim 1, further comprising a control system operatively coupled to each of said channel driving systems, said control system providing selected values for at least one of said amplitude and said phase of said output signal of each of said channel driving systems.

3. The ultrasonic system of claim 2, wherein said control system provides selected values for said amplitude and said phase of said output signal of each of said channel driving systems.

4. The ultrasonic system of claim 1, wherein each channel driving system of said plurality of channel driving systems includes a power measurement system and a phase detector.

5. The ultrasonic system of claim 1, wherein each of said channel driving systems comprises a power converter having a switching amplifier, said power converter producing an AC signal.

6. The ultrasonic system of claim 5, wherein said switching amplifier is a class D/E amplifier.

7. The ultrasonic system of claim 5, wherein each of said channel driving systems further comprises a harmonic filter, said power converter and said harmonic filter producing a substantially single frequency sinusoidal output signal.

8. The ultrasonic system of claim 1, wherein each of said channel driving systems comprises a power regulator operatively coupled to said power measurement system, said power regulator adjusting the amplitude of said output signal based on said pre-selected value of said output signal and the measured amplitude of said output signal.

9. The ultrasonic system of claim 1, wherein each of said channel driving systems further comprises a phase shifter operatively coupled to said phase detector, said phase shifter adjusting the phase of said output signal based on said pre-selected value of output signal and the measured phase of said output signal.

10. The ultrasonic system of claim 1, wherein each of said transducers includes matching circuitry to provide an impedance match between the corresponding channel driving system and the corresponding transducer.

11. An ultrasonic system for selectively and non-invasively vaporizing body tissue, the system comprising:
    an extracorporeal array of ultrasonic transducer elements, each of said transducer elements being capable of producing an ultrasonic wave;
    a plurality of channel driving systems, each of said channel driving systems being coupled to one of said transducer elements and providing an output signal having an amplitude and a phase to said one of said transducer elements; and
    a control system operatively coupled to each of said channel driving systems, said control system providing a selected value of said phase of said output signal of each of said channel driving systems;
    each of said channel driving systems including a phase detector for providing measured value of said phase of said corresponding output signal or of said phase of said corresponding ultrasonic wave, each of said channel driving systems adjusting said corresponding output signal based on said selected value of said phase of said output signal and the measured value of said phase of said output signal or said ultrasonic wave to selectively vaporize said body tissue.

12. The ultrasonic system of claim 11, wherein each of said channel driving systems further includes an amplitude measurement system for measuring the amplitude of said corresponding output signal, and
    wherein said control system provides a selected value of the amplitude of said output signal of each of said channel driving systems, each of said channel driving systems adjusting said corresponding output signal based on said selected value of the amplitude of said output signal and the measured value of the amplitude of said output signal.

13. A method of selectively and non-invasively vaporizing human tissue, the method comprising the steps of:
    providing an ultrasonic system comprising an extracorporeal array of channel driver and ultrasonic transducer pairs for producing an array of ultrasonic waves,
    launching the array of ultrasonic waves at a target tissue site within the body, and
    focusing the ultrasonic waves at the target site by producing constructive interference of the ultrasonic waves at the target site, said focusing resulting in vaporization of tissue at the target site, said focusing including measuring a value of at least one of signal amplitude and phase transmitted to the array of ultrasonic transducers, and adjusting at least one of the amplitude and the phase transmitted to the array of ultrasonic transducers based on the measured value and a corresponding preselected value.

14. The method of claim 13, wherein said step of focusing comprises measuring the value of the signal amplitude and the phase transmitted to the array of ultrasonic transducers, and adjusting the amplitude and the phase transmitted to the array of ultrasonic transducers based on the measured value and a corresponding pre-selected value of the amplitude or phase.

15. The method of claim 13, wherein said step of focusing comprises measuring a value of at least one of signal amplitude and phase trasmitted to each of the ultrasonic transducers, and adjusting at least one of the amplitude and the phase transmitted to each of the ultrasonic transducers based on the measured value and a corresponding preselected value.

16. The method of claim 13, further comprising the steps of selecting values of signal power and of phase for the array of ultrasonic transducers and transmitting the values to the array of ultrasonic transducers.

17. A method of selectively and non-invasively vaporizing human tissue, the method comprising the steps of:

providing an ultrasonic system comprising an extracorporeal array of channel driver and ultrasonic transducer pairs for producing an array of ultrasonic waves, launching the array of ultrasonic waves at a target tissue site within the body, and focusing the ultrasonic waves at the target site by producing constructive interference of the ultrasonic waves at the target site, said focusing resulting in vaporization of tissue at the target site, said focusing including measuring a value of signal phase transmitted to the array of ultrasonic transducers or a value of the phase of the ultrasonic waves, and adjusting signal phase transmitted to the array of ultrasonic transducers based on one of the measured values and a corresponding pre-selected value.

18. The method of claim 17, wherein said step of focusing includes measuring the value of the signal amplitude transmitted to the array of ultrasonic transducers, and adjusting the amplitude transmitted to the array of ultrasonic transducers based on the measured value of the signal amplitude and a corresponding pre-selected value of the signal amplitude.

\* \* \* \* \*